(12) United States Patent
Rockhill et al.

(10) Patent No.: US 12,428,301 B1
(45) Date of Patent: Sep. 30, 2025

(54) GRAPHENE COMPOSITION

(71) Applicants: Alvin T. Rockhill, Akron, OH (US); William E. Lemmon, N. Canton, OH (US)

(72) Inventors: Alvin T. Rockhill, Akron, OH (US); William E. Lemmon, N. Canton, OH (US)

( * ) Notice: Subject to any disclaimer, the term of this patent is extended or adjusted under 35 U.S.C. 154(b) by 816 days.

(21) Appl. No.: 17/704,765

(22) Filed: Mar. 25, 2022

Related U.S. Application Data

(60) Provisional application No. 63/166,442, filed on Mar. 26, 2021.

(51) Int. Cl.
  *C01B 32/182* (2017.01)
  *C07C 53/126* (2006.01)
  *C08K 3/04* (2006.01)
  *C08K 5/09* (2006.01)
  *C08L 57/00* (2006.01)

(52) U.S. Cl.
  CPC .......... *C01B 32/182* (2017.08); *C07C 53/126* (2013.01); *C08K 3/042* (2017.05); *C08K 5/09* (2013.01); *C08L 57/00* (2013.01)

(58) Field of Classification Search
  CPC ... C01B 32/182; C01B 32/184; C01B 32/186; C01B 32/188; C01B 32/19; C01B 32/192; C01B 32/194; C01B 32/196; C01B 32/198; C01B 2204/00; C01B 2204/02; C01B 2204/04; C01B 2204/06; C01B 2204/065; C01B 2204/20; C01B 2204/22; C01B 2204/24; C01B 2204/26; C01B 2204/28; C01B 2204/30; C01B 2204/32; C01B 32/20; C01B 32/205; C01B 32/21; C01B 32/215; C01B 32/22; C01B 32/225; C01B 32/23; C07C 53/126; C08K 3/042; C08K 5/09; C08L 57/00
  See application file for complete search history.

(56) References Cited

U.S. PATENT DOCUMENTS

| | | |
|---|---|---|
| 1,378,172 A | 5/1921 | Gostlin |
| 1,910,128 A | 5/1933 | Semler |
| 2,305,412 A | 12/1942 | Frolich et al. |
| 3,144,374 A | 8/1964 | Saint Paul |
| 3,547,734 A | 12/1970 | Read |
| 3,936,080 A | 2/1976 | Bennett |
| 3,952,840 A | 4/1976 | Yamazaki et al. |
| 3,963,394 A | 6/1976 | Shichman et al. |
| 3,964,807 A | 6/1976 | White |
| 3,967,978 A | 7/1976 | Honda et al. |
| 3,979,249 A | 9/1976 | Nicholls |
| 3,990,930 A | 11/1976 | Schmit |
| 4,030,740 A | 6/1977 | Kniss, Jr. |
| 4,030,863 A | 6/1977 | MacMillan |
| 4,071,994 A | 2/1978 | Ammann |
| 4,235,482 A | 11/1980 | Gibson |
| 4,240,653 A | 12/1980 | Ishigaki |
| 4,241,944 A | 12/1980 | Clark |
| 4,247,838 A | 1/1981 | Sirel |
| 4,249,979 A | 2/1981 | Burley |
| 4,279,533 A | 7/1981 | Peterson et al. |
| 4,310,427 A | 1/1982 | Wun |
| 4,374,442 A | 2/1983 | Heir |
| 4,504,604 A | 3/1985 | Pilkington et al. |
| 4,863,650 A | 9/1989 | Kohler et al. |
| 4,877,469 A | 10/1989 | Szyms et al. |
| 5,044,835 A | 9/1991 | Fukushima |
| 5,062,781 A | 11/1991 | Szyms et al. |
| 5,080,332 A | 1/1992 | Yoda et al. |
| 5,190,269 A | 3/1993 | Keda et al. |
| 5,328,160 A | 7/1994 | McLaughlin |
| 5,538,218 A | 7/1996 | Patitsas et al. |
| 5,580,513 A | 12/1996 | Patitsas et al. |
| 6,176,526 B1 | 1/2001 | McRae et al. |
| 6,231,026 B1 | 5/2001 | Patitsas et al. |
| 7,071,258 B1 | 7/2006 | Jang et al. |
| 7,128,545 B2 | 10/2006 | Wang et al. |
| 7,144,236 B2 | 12/2006 | Wang et al. |
| 8,057,204 B2 | 11/2011 | Agostini et al. |
| 8,142,754 B2 | 3/2012 | Lanzara et al. |
| 8,465,010 B2 | 6/2013 | Kuki et al. |
| 9,249,911 B2 | 2/2016 | Ikeda |
| 9,388,048 B1 | 7/2016 | Zhou et al. |
| 9,631,759 B2 | 4/2017 | Chase et al. |
| 9,739,049 B1 | 8/2017 | Robinson |
| 10,000,384 B2 | 6/2018 | Xu et al. |
| 10,023,727 B2 | 7/2018 | Jung et al. |
| 10,538,041 B2 | 1/2020 | Randall et al. |
| 10,717,653 B2 | 7/2020 | Womble et al. |
| 2010/0124611 A1 | 5/2010 | Mayo et al. |
| 2011/0309336 A1 | 12/2011 | Shin et al. |

(Continued)

OTHER PUBLICATIONS

Stearic Acid, accessed online at https://pubchem.ncbi.nlm.nih.gov/compound/Stearic-Acid on Feb. 8, 2025 (Year: 2025).*

(Continued)

*Primary Examiner* — Daniel C. McCracken
(74) *Attorney, Agent, or Firm* — Alvin T. Rockhill

(57) ABSTRACT

This invention provides a safe, environmentally friendly and solvent free method for dispersing graphene into polymeric compositions. In this process solid particles of graphene in a fatty acid matrix are mixed into the polymeric composition. The use of these solid graphene containing particles does not create dust while being mixed into the polymer and can much more easily be mixed into the polymer. Since fatty acids, such as stearic acid, palmitic acid, and oleic acid, are frequently incorporated into the polymeric formulations used in making a wide variety of products, this technique also offers a good method for introducing the fatty acid into the polymeric formulation. In such fatty acid containing polymeric formulations this technique also offers the advantage of not introducing unwanted solvents or agents into the formulation.

20 Claims, 4 Drawing Sheets

(56) References Cited

U.S. PATENT DOCUMENTS

| | | | |
|---|---|---|---|
| 2012/0145234 A1 | 6/2012 | Roy-Mayhew et al. | |
| 2012/0277360 A1 | 11/2012 | Scheffer et al. | |
| 2013/0150516 A1 | 6/2013 | Lettow | |
| 2014/0034899 A1 | 2/2014 | Ahn et al. | |
| 2014/0225026 A1 | 8/2014 | Park et al. | |
| 2017/0088688 A1 | 3/2017 | Tsou et al. | |
| 2018/0215904 A1* | 8/2018 | Cesareo | B60C 1/0016 |
| 2018/0327611 A1 | 11/2018 | Scheffer et al. | |
| 2019/0040211 A1 | 2/2019 | Chen et al. | |
| 2019/0256701 A1 | 8/2019 | Nakano | |
| 2019/0315909 A1 | 10/2019 | Luesing et al. | |

OTHER PUBLICATIONS

Coran, Vulcanization, Science of Technology of Rubber, Second Ediction, pp. 339-385 (Academic Press 1994) (Year: 1994).*

* cited by examiner

GRAPHENE COMPOSITION

This application claims benefit of U.S. Provisional Patent Application Ser. No. 63/166,442 filed on Mar. 26, 2021. The teachings of U.S. Provisional Patent Application Ser. No. 63/166,442 are incorporated herein by reference in their entirety.

FIELD OF THE INVENTION

This invention relates to a graphene carrier formulation which can be safely and conveniently used in manufacturing polymeric products containing graphene, such as inks, solar cells, light-emitting diodes (LEDs), electronic devices (such as computers, tablets, smart phones), touch screens for electronic devices, tires, hoses, power transmission belts, air springs, bushings, vibration control pads, sporting goods, and a wide variety of other products.

BACKGROUND OF THE INVENTION

Graphene is an allotrope of carbon which is in the form of a single layer of carbon atoms arranged in a two-dimensional honeycomb-shaped lattice. The carbon atoms in graphene sheets are connected to their three nearest neighbors by σ-bonds which contribute one electron to a conduction band that extends over the entire sheet. This is reported to be the same type bonding as in carbon nanotubes and polycyclic aromatic hydrocarbons, such as is in fullerenes and glassy carbon. This type of bonding creates conduction bands which makes graphene a semimetal with charge carriers that exhibit a linear, rather than quadratic, dependence of energy on momentum. In any case, graphene is an excellent conductor of heat and electricity. Graphene also strongly absorbs wavelengths of light over its entire visible spectrum which makes it black in color. On the other hand, single sheets of graphene are essentially transparent because of their extreme thinness. By virtue of graphene being a transparent and flexible conductor of heat and electricity it is exceptionally useful in manufacturing solar cells, light-emitting diodes (LEDs), smart phones and a wide variety of other electronic devices. It has proven to be exceptionally useful in making touch screens for tablets, computer monitors, and smart phones.

Graphene also offers a wide array of unique and desirable physical characteristics. For instance, sheets of graphene are approximately 100 times stronger than the strongest known steels of the same thickness. It can also be incorporated into polymeric compositions to increase their strength, abrasion resistance, flex characteristics, heat conductivity, and electrical conductivity. More specifically, graphene can be incorporated into plastics, thermoplastic elastomers, and thermosetting elastomers, such as natural and synthetic rubber, to improve the chemical and physical properties of the material. Many of these graphene containing compositions also contain one or more fatty acids, such as stearic acid, palmitic acid, or oleic acid.

United States Patent Application Publication No. 2010/0124611 A1 describes a phase change ink including a phase change ink carrier, graphene as a colorant, and stearic acid. The ink can be selected from paraffins, microcrystalline waxes, polyethylene waxes, ester waxes, amides, fatty acids, fatty amide containing materials, sulfonamide materials, resinous materials made from natural sources, synthetic resins, oligomers, polymers, and copolymers.

United States Patent Application Publication No. 2018/0327611 A1 describes a conductive composition comprising graphene sheets, graphite, carbon black, and stearic acid wherein the graphene sheets are present in about 0.2 to about 10 weight percent relative to the total weight of graphene sheets, graphite, and carbon black. This document also reveals a conductive ink or coating comprising: a composition having graphene sheets, graphite, and carbon black, wherein the graphene sheets are present in about 0.2 to about 10 weight percent relative to the total weight of graphene sheets, graphite, and carbon black. It further discloses an article coated with the conductive ink or coating wherein the conductive ink or coating is formed on the article as a film, a line, a pattern, a letter, a number, a circuit, a logo, an identification tag, a printed circuit, and/or a sensor. The article can be a film, a cellulose-based material, a three-dimensional object, or a metal.

United States Patent Application Publication No. 2014/0034899 A1 discloses a graphene semiconductor comprising: graphene; and a metal atomic layer disposed on the graphene, wherein the metal atomic layer comprises a metal, which is capable of charge transfer with the graphene. The metal atomic layer of the graphene semiconductor is comprised of an alkali metal, such as sodium and the metal atomic layer is disposed on a surface of the graphene. The metal atomic layer of the graphene semiconductor can be comprised of a two-dimensional film structure.

United States Patent Application Publication No. 2011/0309336 A1 discloses a graphene composition comprising: a graphene monolayer; and an alkali metal disposed on the graphene monolayer. This publication further reveals an electrical device comprising the graphene composition wherein the electrical device is a sensor, a bipolar junction transistor, a field effect transistor, a heterojunction bipolar transistor, a single electron transistor, a light emitting diode, and an organic electroluminescent diode.

United States Patent Application Publication No. 2012/0145234 A1 discloses electrodes for dye-sensitized solar cells comprising graphene sheets and at least one binder, wherein the electrodes may be conductive electrodes or catalytic counter electrodes, and wherein the electrodes may be flexible. This publication further describes a dye-sensitized solar cell comprising the electrode wherein the solar cell is in the form of a monolithic solar cell.

United States Patent Application Publication No. 2012/0277360 discloses a coating composition comprising graphene sheets, at least one binder, at least one polyalkyleneimine, and at least one liquid carrier. The carrier can be a terpene, one or more alcohols, and one or more glycol ethers, or a combination thereof and the binder is at least one polyamide. This publication further reveals a method for coating a substrate comprising applying the coating to the substrate, wherein the substrate is glass, such as a glass lens.

United States Patent Application Publication No. 2019/0315909 A1 discloses a cast polyurethane elastomer including graphene nano-platelets and a process for preparing such cast elastomers. This cast elastomer is comprised of a reaction product of: (A) 10 weight percent to 98 percent of at least one isocyanate component, (B) 2 weight percent to 90 weight percent of at least one polyol component, (C) 0.1 weight percent to 20 weight percent of graphene nano-platelets having an average lateral dimension (x, y) in a range of 1 μm to 100 μm determined by atomic force microscope, an average through-plane dimension (z) in a range of 5 nm to 100 nm determined by atomic force microscope and an oxygen content in a range of 0.01 weight percent to 10 weight percent, based on a total weight of the graphene, nano-platelets, and (D) 1 weight percent to 30 weight percent of at least one cross-linker or a chain extender, wherein the weight percent is based on a total weight of the cast elastomer and wherein the cast elastomer has a hard segment content in a range of 50% to 97%, the hard segment content being defined by a formula:

$$\text{Hard segment content} = \{\Sigma x{-}1^n[m_{CE}/EW_{CE}]/[m_{ICN}/EW_{ICN}]\} \times 100\%$$

wherein $m_{CE}$ is a mass of the at least one cross linker or the chain extender in g, $EW_{CE}$ is an equivalent weight of the at least one cross linker or the chain extender in g/eq, $m_{ICN}$ is a mass of the at least one isocyanate component in g, $EW_{ICN}$ is an equivalent weight of the at least one isocyanate component in g/eq, and n is a number of cross linker or chain extender and the isocyanate. United States Patent Application Publication No. 2019/0315909 A1 also reveals a process for preparing such a cast elastomer, comprising the steps of: (A') preparing an isocyanate prepolymer comprising the at least one isocyanate component (A), the at least one polyol component (B) and the graphene nano-platelets (C), wherein the isocyanate prepolymer has an isocyanate index in a range of 1 to 300, and (B') reacting the isocyanate prepolymer of step (A') with the at least one cross-linker or the chain extender (D) to obtain a cast elastomer having a hard segment content in a range of 50% to 97%, the hard segment content being defined by a formula:

$$\text{Hard segment content} = \{\Sigma x{-}1^n[m_{CE}/EW_{CE}]/[m_{ICN}/EW_{ICN}]\} \times 100\%$$

wherein, $m_{CE}$ is a mass of the at least one cross linker or the chain extender in g, $EW_{CE}$ is an equivalent weight of the at least one cross linker or the chain extender in g/eq, $m_{ICN}$ is a mass of the at least one isocyanate component in g, $EW_{ICN}$ is an equivalent weight of the at least one isocyanate component in g/eq, n is a number of cross linker or chain extender and the isocyanate, wherein the graphene nano-platelets (C) have an average lateral dimension (x, y) in a range of 1 μu·m to 100 μm determined by atomic force microscope, an average through-plane dimension (z) in a range of 5 nm to 100 nm determined by atomic force microscope and an oxygen content in a range of 0.01 weight percent to 10 weight percent, based on a total weight of the graphene nano-platelets (C).

United States Patent Application Publication No. 2014/0225026 A1 relates to polyamide composites containing graphene, a method for producing them and to their use as or for producing a material with gas barrier and/or electro-conductive and/or thermally conductive properties and/or a mechanically reinforced material. It more specifically describes a method for producing polyamide composites containing graphene, comprising the following steps: (i) dispersing a graphitic or graphenic material in an aqueous medium to yield an exfoliated material, and optionally removing non-reacted starting material from the aqueous mixture; (ii) mixing at least one lactam monomer with the aqueous mixture obtained in step (i); (iii) adding at least one non-ionic surfactant to the aqueous mixture obtained in step (ii); (iv) removing from the aqueous mixture obtained in step (iii) essentially all water contained therein; (v) heating the mixture obtained in step (iv) to 100 to 200.degree. C.; (vi) if the water content of the mixture obtained in step (v) is higher than 300 ppm, subjecting the mixture obtained in step (v) to a further drying process to obtain a mixture with a water content of at most 300 ppm; (vii) heating the mixture obtained in step (v) or (vi) to 100° C. to 200° C.; (viii) adding an anionic polymerization activator; (ix) adding an anionic polymerization catalyst; and (x) after polymerization is completed, isolating the resulting polyamide composite.

United States Patent Application Publication No. 2019/0256701 A1 discloses an acrylic rubber composition having higher tensile properties and higher heat resistance and a vulcanizate thereof. These acrylic rubber compositions include 0.1 to 50 parts by mass of a carbon material including graphene oxide, relative to 100 parts by mass of an acrylic rubber. These acrylic rubbers and vulcanizates thereof have excellent physical properties including heat aging resistance, oil resistance, mechanical characteristics, and permanent compression set characteristics and thus are typically used as materials including hose members, sealing members, and rubber vibration isolator members in an automobile engine compartment. Such members are also required to have more excellent physical properties including tensile properties and heat resistance to meet recent demands including emission controls and higher engine power.

United States Patent Application Publication No. 2019/0040211 A1 discloses elastomer compounds comprising: at least one elastomer that is resistant to heat for 70 hours at 100° C. such that the at least one elastomer exhibits at least one of the following properties selected from: (a) a change in durometer hardness of no more than 15 points, (b) a change in tensile strength of no more than 40%, and (c) a change in ultimate elongation of no more than 40%. The elastomer compound further comprises at least one graphene-based material present in an amount ranging from 0.01 phr to 30 phr relative to the at least one elastomer and at least one carbon black present in an amount ranging from 15 phr to 150 phr relative to the at least one elastomer. This document indicates that the elastomer compounds disclosed herein can be used in the manufacture of various articles in sealing, insulation, vibration damping, and fluid delivery applications. Exemplary articles include o-ring seals and sealants, gaskets, diaphragms, valves, hydraulic seals, swell packers, blow out preventers, oil resistant hose liners. Other examples of articles include those used under the hoods of automobiles where the articles may operate at high temperatures, and to perform cooler, high thermal conductivity is desirable to dissipate heat effectively. Such articles include wire harnesses, battery cables, turbo hoses, molded air ducts, brake parts, grommets, hydraulic and radiator hoses, transmission seals and gaskets, engine and chassis vibration mounts, constant velocity joint boots, engine seals, and fuel system components. These and other articles can have applications in the oil/gas, aerospace, and automotive industries. The articles disclosed herein can have beneficial properties to enhance one or more of high sealing efficiency at service temperature, high rapid gas decompression (RGD) resistance, and high extrusion resistance.

United States Patent Application Publication No. 2013/0150516 A1 discloses rubber compositions comprising graphene sheets, at least one reinforcing agent, and at least one rubber. These compositions may further comprise carbon black and may be formed into a variety of rubber articles, including tires, such as in tire treads, tire belts, tire sidewalls, tire inner liners, and the like. These tires may be non-pneumatic tires and pneumatic tires, including radial tires, bias ply tires, tubeless tires, solid tires, run-flat tires, and the like. For examples, the tires may be used in motorized vehicles, equipment, and accessories such as automobiles, trucks, racing vehicles, motorcycles, mopeds, all-terrain vehicles, golf carts, off-read vehicles, construction equipment, earthmovers, dump trucks, lawn mowers, farm equipment, tractors, harvesters, trailers, wheelchairs, aircraft, forklifts, lift trucks, tanks, aviation (such as airplanes, helicopters, etc.), and the like. These tires may be used in non-motorized motorized vehicles, equipment, and accessories such as bicycles, tricycles, unicycles, wheelchairs, wheel barrows, carts, and the like. These rubber compositions can also be used in footwear, such as including boots, athletic shoes, safety shoes, dress shoes, including footwear soles. These rubber compositions are also reported to be useful in seals, cables, profiles, hoses, industrial rubber goods, belts, conveyer belts, power transmission belts, rollers, floor coverings, golf balls, windows, vibration control applications (such as earthquake protection equipment (such as rubber bearings), floors, walls, windows, helicopter vibration dampeners, engine mounts, belts (including timing belts, drive belts, transmission belts, etc.), airsprings, seals, hoses, tubes, cables, and the like.

United States Patent Application Publication No. 2018/0215904 A1 discloses elastomeric composition for producing tire components comprising, based upon parts by weight per 100 parts by weight of rubber (phr): (A) 100 phr of a blend of rubber comprising at least 20% by weight of an isoprene polymer; (B) from 0 to 30 phr of silica; (C) from 0 to 50 phr of amorphous carbon black; (D) from 1 to 40 phr of graphene, wherein the graphene consists of graphene nanoplatelets, wherein at least 90% have a lateral size (x, y) from 50 to 50000 nm and a thickness (z) from 0.34 to 50 nm, wherein the lateral size is always greater than the thickness (x, y>z), and wherein the C/O ratio is .gtoreq.100:1.

As heretofore described, it is known that graphene can be incorporated various polymeric compositions to improve the chemical, electrical, thermal, and mechanical properties thereof. However, graphene is difficult to homogeneously incorporate into such elastomers. This is because graphene is an extremely fine powder and it requires sufficient favorable enthalpic contributions to overcome the entropic penalties needed to attain good mixing. Fine graphene dust can also present an explosion hazard and potentially environmental problems when used in large scale in industrial applications. In any case, it has thus proven to be very difficult to disperse graphene into generally inert, nonpolar, rubbery polymers. This problem is appreciated by United States Patent Application Publication No. 2017/0088688 wherein a graphene is incorporated into a halobutyl rubber through a nanofiller dispersant composition comprising: (a) the reaction product of: (i) at least one halogenated copolymer comprising units derived from isoolefins having from 4 to 7 carbons and a para-alkylstyrene; and (ii) at least one polycyclic aromatic hydrocarbon (PAH); and (b) graphene. It is also known in the prior art to disperse graphene into a volatile hydrocarbon solvent and then to subsequently mix the dispersion into a polymeric composition with the volatile hydrocarbon solvent then being removed by volatilization of the solvent. In any case, there remains to be a need for a better procedure for dispersion graphene into polymeric compositions.

SUMMARY OF THE INVENTION

This invention provides a safe, environmentally friendly and solvent free method for dispersing graphene into polymeric compositions. In this process solid particles of graphene in a fatty acid matrix is mixed into the polymeric composition. The use of these solid graphene containing particles does not create dust while being mixed into the polymer and can much more easily be mixed into the polymer. Since fatty acids, such as stearic acid, palmitic acid, and oleic acid, are frequently incorporated into the polymeric formulations used in making a wide variety of products this technique also offers a good method for introducing the fatty acid into the polymeric formulation. In such fatty acid containing polymeric formulations this technique also offers the advantage of not introducing unwanted solvents or agents into the formulation.

The solid particles of graphene in a fatty acid matrix used in the practice of this invention can be made by simply mixing the graphene into the fatty acid or mixture of fatty acids at a temperature which is above the melting point of the fatty acid. The dispersion of the graphene in the fatty acid is then cooled to below the melting point of the fatty acid to form a solid composition which can be ground into particles of the desired size range. For instance, the solid composition can be ground into particles having the consistence of sand.

The present invention more specifically discloses a graphene composition comprising graphene and a fatty acid containing from 18 to 24 carbon atoms and having a melting point which is above about 140° F. (60° C.), wherein the graphene composition contains from about 0.25 parts by weight to 10 parts by weight of graphene per part by weight of the fatty acid, and wherein the graphene composition is in the form of particles.

The subject invention also reveals a graphene composition which consists essentially of graphene, a fatty acid containing from 18 to 24 carbon atoms and having a melting point which is above about 140° F. (60° C.), optionally an alkyl lactate having an alkyl group containing from 2 to 8 carbon atoms, and optionally zinc oxide, wherein the graphene composition contains from about 0.25 parts by weight to 10 parts by weight of graphene per part by weight of the fatty acid.

The subject invention further reveals a method for making a graphene composition which comprises (1) mixing the graphene into the fatty acid or mixture of fatty acids containing from 18 to 24 carbon atoms at a temperature which is above the melting point of the fatty acid; (2) dispersing of the graphene into the fatty acid to produce a liquid dispersion; (3) cooling the liquid dispersion to below the melting point of the fatty acid to form a solid composition; and (4) grinding the solid composition into particles of graphene composition having the desired particle size range.

The subject invention also reveals a method for making a graphene composition which comprises (1) mixing the graphene into the fatty acid or mixture of fatty acids containing from 18 to 24 carbon atoms at a temperature which is above the melting point of the fatty acid; (2) dispersing of the graphene into the fatty acid to produce a liquid dispersion; and (3) cooling the liquid dispersion to below the melting point of the fatty acid under agitation to form a solid particle composition.

The present invention also discloses a method for dispersing graphene into a polymeric formulation which comprises mixing a graphene composition into the polymeric formulation, wherein the graphene composition is comprised of graphene and a fatty acid containing from 18 to 24 carbon atoms and having a melting point which is above about 140° F. (60° C.), wherein the graphene composition contains from about 0.25 parts by weight to 10 parts by weight of graphene per part by weight of the fatty acid, and wherein the graphene composition is in the form of particles, and wherein the mixing is conducted at a temperature which is above the melting point of the fatty acid.

DETAILED DESCRIPTION OF THE INVENTION

Figure 1:
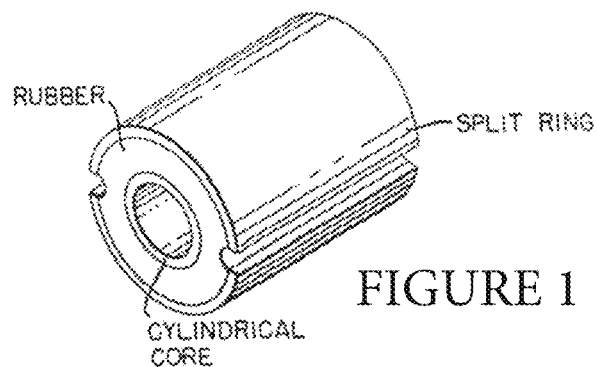
FIG. 1 illustrates a split ring tubular bushing.

The graphene compositions of this invention are made by dispersing graphene into a fatty acid containing from 18 to 24 carbon atoms and having a melting point which is above about 140° F. (60° C.), such as stearic acid or palmitic acid, or a mixture of such fatty acids. The fatty acid will typically contain from 18 to 20 carbon atoms and with more typically contain from 17 to 19 carbon atoms. The fatty acid will preferably contain 18 carbon atoms, such as stearic acid or palmitic acid.

In making the graphene compositions of this invention the fatty acid or fatty acid mixture is heated to a temperature which is above its melting point. Steric acid (CAS No. 57-11-4) has a melting point of 157° F. (63° C.) and palmitic acid (CAS No. 57-10-3) has a melting point of 145° F. (63° C.). Accordingly, the fatty acid will typically be heated to a temperature which is within the range of about 157° F. (63° C.) to about 250° F. (121° C.). The fatty acid will more typically be heated to a temperature which is within the range of 160° F. (71° C.) to 220° F. (104° C.) and will usually be heated to a temperature which is within the range of 165° F. (74° C.) to 200° F. (93° C.).

After the fatty acid is molten the graphene is mixed into it. This can be accomplished utilizing a conventional mixing technique which is suitable for mixing a solid material into a liquid. Normally from about 0.25 parts by weight to 10 parts by weight of graphene will be mixed into the fatty acid per part by weight of the fatty acid. More typically from about 0.5 parts by weight to 8 parts by weight of graphene will be mixed into the fatty acid. In most cases from about 1 part by weight to 6 parts by weight of graphene will be mixed into the fatty acid. It is often preferred to mix from about 1 part by weight to 3 parts by weight of graphene will be mixed into the fatty acid. To attain particles having a good consistency at higher levels of graphene loading (over about 3 parts by weight per part by weight of the fatty acid) it is desirable to further mix an alkyl lactate having an alkyl group containing from 2 to 8 carbon atoms into the molten fatty acid. Some representative examples of alkyl lactates that can be used include ethyl lactate, iso-propyl lactate, n-propyl lactate, iso-butyl lactate, n-butyl lactate, t-butyl lactate, and isoamyl lactate. In is normally preferred to used isoamyl lactate. In any case, if an alkyl lactate is optionally used it will generally be added at a level of 0.01 parts to 2 parts per parts by weight of the fatty acid. The alky lactate will more typically be added at a level which is with the range of 0.05 parts to 1 part per parts by weight of the fatty acid. It is normally preferred to utilize the alkyl lactate at a level which is within the range of 0.1 parts to 0.5 parts by weight per part by weight of the fatty acid.

After the graphene has been mixed throughout the molten fatty acid, preferably to attain an essentially homogeneous dispersion, the dispersion is cooled to a temperature which is below the melting point of the fatty acid. Typically, the dispersion will be cooled to a temperature which is within the range of 50° F. (10° C.) to 90° F. (32° C.) and which is more typically within the range of 60° F. (16° C.) to 80° F. (27° C.). It can be desirable to additionally shearing forces to the dispersion as it is being cooled to attain the desired particle size for the graphene composition. In an alternative embodiment the molten dispersion can be extruded and cooled into filaments or strips which can subsequently be pulverized into particles of the desired size. For example, the graphene mixture can ground into particles which are easy to handle and to mix into polymeric formulations.

In a preferred embodiment of this invention the molten dispersion of graphene in the fatty acid is continually mixed as it is being cooled to form a solid graphene dispersion. This results in the formation of relatively fine non-dusting particles. In practicing this embodiment of the invention at least about 2 parts by weight of graphene per part by weight of the fatty acid will be incorporated into the graphene dispersion at facilitate adequate mixing. In most cases from about 2 parts by weight to 10 parts by weight of graphene is mixed into 1 part by weight of the fatty acid. It is typically preferred for such graphene dispersions to contain from about 3 parts by weight to 8 parts by weight of graphene per part by weight of the fatty acid. For instance, such graphene dispersions can contain from about 3 parts by weight to 6 parts by weight of graphene per part by weight of the fatty acid.

The graphene composition of this invention can be easily mixed into a wide variety of polymeric materials. For instance, it can be mixed into plastics, thermoplastic elastomers, natural rubber, and a wide variety of synthetic rubbers. It is of particular value when used in making polymer formulations where it is also desired to include a fatty acid. Using it is a convenient way to add both the graphene and the fatty acid to the polymer. Of course, additional quantities of the fatty acid can be separately added the polymer formulation in the event that the desired level is not attained by the addition of the graphene composition of this invention by itself. In other words, fatty acids can be added to the polymer formulation separately to attain a desired graphene to fatty acid ratio.

Coating compositions containing both graphene and stearic acid can be made in accordance with the teachings of United States Patent Application Publication No. 2012/0277360 utilizing the graphene compositions of this invention. These coating compositions can also be used in coating glass, such as glass lenses. The teachings of United States Patent Application Publication No. 2012/0277360 are incorporated herein by reference.

Cast urethane elastomers containing both graphene and stearic acid can be made in accordance with the teachings of United States Patent Application Publication No. 2019/0315909 A1 utilizing the graphene compositions of this invention. The teachings of United States Patent Application Publication No. 2019/0315909 A1 are incorporated herein by reference.

Polyamide composites containing both graphene and stearic acid can be made in accordance with the teachings of United States Patent Application Publication No. 2014/0225026 A1 utilizing the graphene compositions of this invention. The teachings of United States Patent Application Publication No. 2014/0225026 A1 are incorporated herein by reference.

Acrylic rubber compositions containing both graphene and stearic acid can be made in accordance with the teachings of United States Patent Application Publication No. 2019/0256701 A1 utilizing the graphene compositions of this invention. The teachings of United States Patent Application Publication No. 2019/0256701A1 are incorporated herein by reference.

Elastomer compounds containing both graphene and stearic acid can be made in accordance with the teachings of United States Patent Application Publication No. 2019/0040211 A1 utilizing the graphene compositions of this invention. These elastomer compounds can be used in the manufacture of various articles in sealing, insulation, vibration damping, and fluid delivery applications. Exemplary articles include o-ring seals and sealants, gaskets, diaphragms, valves, hydraulic seals, swell packers, blow out preventers, oil resistant hose liners. Other examples of articles include those used under the hoods of automobiles where the articles may operate at high temperatures, and to perform cooler, high thermal conductivity is desirable to dissipate heat effectively. Such articles include wire harnesses, battery cables, turbo hoses, molded air ducts, brake parts, grommets, hydraulic and radiator hoses, transmission seals and gaskets, engine and chassis vibration mounts, constant velocity joint boots, engine seals, and fuel system components. These and other articles can have applications in the oil/gas, aerospace, and automotive industries. The articles disclosed herein can have beneficial properties to enhance one or more of high sealing efficiency at service temperature, high rapid gas decompression (RGD) resistance, and high extrusion resistance. The teachings of United States Patent Application Publication No. 2019/0040211 A1 are incorporated herein by reference.

Rubber compositions containing both graphene and stearic acid can be made in accordance with the teachings of United States Patent Application Publication No. 2013/0150516 A1 utilizing the graphene compositions of this invention. These compositions may further comprise carbon black and may be formed into a variety of rubber articles, including tires, such as in tire treads, tire belts, tire sidewalls, tire inner liners, and the like. These tires may be non-pneumatic tires and pneumatic tires, including radial tires, bias ply tires, tubeless tires, solid tires, run-flat tires, and the like. For examples, the tires may be used in motorized vehicles, equipment, and accessories such as automobiles, trucks, racing vehicles, motorcycles, mopeds, all-terrain vehicles, golf carts, off-read vehicles, construction equipment, earthmovers, dump trucks, lawn mowers, farm equipment, tractors, harvesters, trailers, wheelchairs, aircraft, forklifts, lift trucks, tanks, aviation (such as airplanes, helicopters, etc.), and the like. These tires may be used in non-motorized motorized vehicles, equipment, and accessories such as bicycles, tricycles, unicycles, wheelchairs, wheel barrows, carts, and the like. These rubber compositions can also be used in footwear, such as boots, athletic shoes, safety shoes, dress shoes, including footwear soles. These rubber compositions are also reported to be useful in seals, cables, profiles, hoses, industrial rubber goods, belts, conveyer belts, power transmission belts, rollers, floor coverings, golf balls, windows, vibration control applications (such as earthquake protection equipment (such as rubber bearings), floors, walls, windows, helicopter vibration dampeners, engine mounts, belts (including timing belts, drive belts, transmission belts, etc.), airsprings, seals, hoses, tubes, cables, and the like. The teachings of United States Patent Application Publication No. 2013/0150516 A1 are incorporated herein by reference.

Elastomer compositions containing both graphene and stearic acid can be made in accordance with the teachings of United States Patent Application Publication No. 2013/0150516 A1 utilizing the graphene compositions of this invention. The teachings of United States Patent Application Publication No. 2013/0150516 A1 are incorporated herein by reference.

In one specific embodiment of this invention the graphene composition can be used in manufacturing cure bladders for manufacturing rubber products. Conventionally, pneumatic rubber vehicle tires are produced by molding and curing a green, or uncured and unshaped, tire in a molding press in which the green tire is pressed outwardly against a mold surface by means of an inner fluid expandable bladder. By this method the green tire is shaped against the outer mold surface which defines the tire's tread pattern and configuration of sidewalls. By application of heat the tire is cured. Generally, the bladder is expanded by internal pressure provided by a fluid such as hot gas, hot water and/or steam which also participates in the transfer of heat for curing or vulcanization purposes. The tire is then allowed to cool somewhat in the mold, sometimes aided by adding cold or cooler water to the bladder. Then the mold is opened, the bladder collapsed by removal of its internal fluid pressure and the tire removed from the tire mold. Such use of the tire curing bladders is well known to those having skill in such art.

Conventionally pneumatic rubber vehicle tires are produced by molding and curing a green or uncured and unshaped tire in a molding press. The green tire is pressed outwardly against a mold surface (sometimes called a negative mold surface) by means of an inner fluid-expandable bladder. By this method the green tire is shaped against the outer mold surface which defines the tire tread pattern and configuration of the side-walls. By application of heat and pressure the tire is molded and cured at elevated temperatures.

In general practice, the expansion of the bladder is accomplished by application of internal pressure to the inner bladder cavity which is provided by a fluid such as gas, hot water and/or steam which also participates in the transfer of heat for the curing or vulcanization of the tire. The tire after molding and curing is allowed to cool somewhat in the mold, sometimes aided by adding cold or cooler water to the bladder. Then the mold is opened, the bladder is collapsed by removal of its internal fluid pressure and the tire is removed from the tire mold. Such use of tire curing bladders is well known to those having skill in the art.

It is recognized that there is substantial relative movement between the outer contacting surface of the bladder and the inner surface of the tire during the expansion phase of the bladder. Likewise, there is considerable relative movement between the outer contacting surface of the bladder and the cured inner surface of tire during the collapse and the stripping of the bladder from the tire after the tire has been molded and vulcanized.

The bladder surface can tend to stick to a tire inner surface after the tire is cured and during the bladder collapsing part of the tire cure cycle. This adhesion may cause roughening of the bladder surface if it is not controlled. This reduces bladder durability and can produce defective tires. For this reason, it is conventional practice to precoat the inner surface of the green or uncured tires with a lubricant in order to provide lubricity between the outer bladder surface and inner tire surfaces during the entire molding operation. This lubricant has also been called a bladder lubricant, and is often a silicone polymer dispersed in a solvent or water.

It is to be appreciated that the release of the tire from its cure bladder in an industrial manufacturing setting is intimately associated with both the phenomenon of release (to prevent sticking) and the phenomenon of lubrication (to enhance slipping) between the bladder and the adjacent tire surfaces. The release aspect refers to the basic ability to avoid adhesion, or release and the aspect of lubrication relates to enhancing the ability of the surfaces to slip and enable a movement of the bladder with respect to the tire.

Butyl rubber is commonly used in tire curing bladders. Butyl rubber is a copolymer of predominantly isobutylene with small amounts of diene monomers, usually isoprene to give sufficient unsaturation to allow the butyl rubber to be crosslinked. Copolymers of isobutylene and para-methyl-styrene which are subsequently brominated are being manufactured and sold by Exxon Mobil. These polymers are useful in many applications where butyl rubber is used.

U.S. Pat. No. 1,378,172 describes an early and primitive bladder curing process in which the exterior of the carcass was not confined within a mold. In this method the carcass and the inner bladder (which resembles a conventional inner tube) are placed on a sectional base ring having annular shoulders to hold the bead portions of the carcass in place and having a central annular groove adapted to receive the inner edge of the bladder accurately centered in place. The bladder is inflated to round out the carcass and maintain it under proper tension while being cured. This method lacks the precision and reproducibility of the configurations now demanded in manufacturing tires and other rubber products as well as requiring an economically unacceptable amount of time and labor to cure the rubber product, such as a tire carcass.

U.S. Pat. No. 1,910,128 describes the use of an air bladder or inner tube which has incorporated therein a heating element to apply heat to the inside of a tire carcass while the latter, encased in a mold, is being cured in a steam kettle.

U.S. Pat. No. 2,305,412 describes the use of a fabric reinforced air bag resembling an inner tube which is inflated within a tire carcass during the curing process.

U.S. Pat. No. 3,144,374 teaches the use of a cylindrical membrane reinforced with spring steel wires and adapted to be stretched between the flanges of the drum of a tire building machine. The membrane can be deformed to a toroidal shape for constructing uncured tire carcasses. The membrane has limited extensibility in the axial direction of the cylinder due to the limited extensibility of the metal wire reinforcement. In one embodiment the reinforcement comprises a plurality of undulating wires i.e. wires having a sine wave configuration. This membrane is not designed for use in a curing process.

U.S. Pat. No. 3,547,734 describes a tire building (as opposed to tire curing) air bag fabricated from multiple layers of rubber which have sandwiched therein a reinforcing layer of cords forming a lattice-work pattern with cords aligned in one direction overlapping cords aligned in a different direction, the angle at which the layers of cord cross each other being as much as 45°.

U.S. Pat. No. 3,963,394 teaches an expandable bladder for shaping radial ply uncured tire carcasses which has a relatively thick center section and a multiplicity of thinner convolutions. This design provides controlled amounts of extensibility axially. Reinforcing material which can be aramid or steel cords is provided through the center section and end sections of the bladder.

U.S. Pat. No. 3,979,249 describes an inflatable air bag for tire building machines which has inextensible reinforcing elements, comprising steel, glass fiber and like cords, in part of the width thereof to limit the expansion of the bag in the reinforced areas thereby controlling the shape which the bag assumes upon inflation.

U.S. Pat. No. 3,990,930 shows a bladder for use with a tire building drum. The bladder is prepared by first forming a partially cured membrane reinforced with parallel cords running axially. The central portion of the membrane is expanded and has a circumferentially extending belt, optionally reinforced with lattice type material.

U.S. Pat. No. 4,030,863 is concerned with providing a separate venting retainer for a cylindrical tire curing bladder. The retainer comprises a net-like cylinder which surrounds the exterior of the bladder and permits escape of air trapped between the inner surface of the tire carcass and the exterior surface of the expanded bladder during the curing operation.

U.S. Pat. No. 4,249,979 describes a fabric reinforced inflatable bladder provided with a ply-folding wedge on its surface and adapted to fold the edges of unvulcanized rubberized ply material around bead wire bundles and the like in the process of building a tire.

U.S. Pat. No. 4,863,650 discloses the use of fillers such as kaolin, chalk, rock dust, silicas, carbon black and graphite in silicone release agent films to result in mat finishes. U.S. Pat. No. 4,310,427 discloses the use of dry powders such as mica, talc, and graphite which were dusted onto the interior surfaces of "green" tires to provide lubrication and release. U.S. Pat. No. 3,967,978 discloses the use of fine solid particles such as mica or graphite in the lubricant.

U.S. Pat. No. 4,877,469 describes a tire curing bladder having controlled stretch characteristics. This curing membrane bladder in the uninflated condition, comprises a cylindrical membrane of rubber having embedded therein a layer of reinforcing material and which, in the inflated condition when used in a tire curing assembly, assumes a toroidal cross-sectional profile; said reinforcing material comprising a plurality of cords which, in the uninflated condition of said bladder, transverse parallel spiral paths within said cylinder of rubber and which, in the said inflated condition of said bladder, are aligned substantially in the direction of the longitudinal axis of said bladder.

U.S. Pat. No. 5,062,781 discloses a tire processing bladder comprising a hollow, tubular relatively thin member having a tubular circumference extending around a tubular axis, said tubular membrane member inflatable to provide a circular circumference greater than the tubular circumference, said tubular membrane member having included therein a plurality of parallel cords, each said cord traversing a spiral path from one end to an opposing end of said tubular membrane at an angle of inclination with respect to the tubular axis, the relative thinness of said tubular membrane member permitting said cords to protrude from said tubular membrane member when formed to have said circular circumference to create reciprocal shallow areas between said cord lengths and thus form a matrix for venting air trapped between said tubular membrane member and an uncured tire, the inclination angle of said cords limiting the circular circumference by limiting the amount said tubular membrane member may be inflated, said tubular membrane member rotating substantially in a screw manner upon inflation into relatively close engagement with an inside surface of said uncured tire. U.S. Pat. No. 5,062,781 further describes a tire processing bladder responsive to the introduction of fluid thereto under a range of fluid pressures for assuming a relatively uninflated state for insertion into a tire processing assembly and a relatively inflated state during tire processing carried out in said assembly, said bladder comprising a tubular shaped membrane of rubber formed along a tubular axis and having embedded therein a plurality of reinforcing cords traversing substantially parallel paths within said rubber in a generally spiral pattern about said tubular axis, and which cords as said bladder is inflated from said relatively uninflated towards said relatively inflated state by said introduction of fluid tend to become aligned away from said spiral pattern and more towards a longitudinal direction aligned with said tubular axis, said bladder forming a substantially toroid-shaped portion inside a tire being cured in said relatively inflated state inside said tire processing assembly, said substantially toroid-shaped portion tending to rotate into relatively close engagement with an inside surface of said tire being cured in response to said introduction of fluid, said cords protruding from said bladder when formed to have said substantially toroid-shaped portion to create reciprocal shallow areas between said cords and thus form a matrix for venting air trapped between said bladder and an uncured tire.

U.S. Pat. No. 5,538,218 discloses an expandable curing bladder consisting essentially of a formulated rubber composition and from about 0.1 to about 30 parts by weight of graphite dispersed throughout said formulated rubber composition, said formulated rubber composition comprising: one or more rubbery polymers including one or more isobutylene rubbery polymers, wherein said isobutylene rubbery polymers are at least 50 weight percent isobutylene units, and are present as at least 50 weight percent of the rubbery polymers of said bladder and one or more curatives for said one or more isobutylene rubbery polymers, wherein said parts by weight are based upon 100 parts by weight of said one or more rubbery polymers in said bladder and wherein said formulated rubber composition after curing and after aging at 177° C. for 24 hours has an elongation at break of from 300% to 700%.

U.S. Pat. No. 5,580,513 discloses an expandable curing bladder being the molded crosslinkstar from a formulation comprising: (1) one or more rubbery polymers, wherein at least 50 weight percent of said rubbery polymers are at least one isobutylene rubbery polymer having at least 80 weight percent units from isobutylene; wherein at least 10 weight percent of said at least one isobutylene rubber polymer is one or more copolymers of isobutylene and para-alkylstyrene; (2) from about 1 to about 20 phr of corn oil dispersed throughout said bladder and wherein said corn oil reduces the Hot Peel Adhesian value of said crosslinked bladder formulation at least 10 percent as compared to the same bladder formulation without said corn oil; and (3) one or more curatives for said rubbery polymers; wherein phr is parts by weight based upon 100 parts by weight of said one or more rubbery polymers in said bladder.

U.S. Pat. No. 6,231,026 describes an expandable bladder of a butyl rubber composition comprised of a formulated rubber composition which contains about 2 to about 10 parts by weight, per 100 parts by weight rubbery polymers in said rubber composition, of lecithin material dispersed throughout said rubber composition selected from at least one of lecithin, acrylated lecithin, hydroxylated lecithin, de-oiled lecithin, said formulated rubber composition comprising: (a) butyl rubber as one or more isobutylene rubbery polymers, wherein said isobutylene rubbery polymers are comprised of from about 80 to about 99 weight percent repeat units from isobutylene and from 1 to about 20 weight percent repeat units from (1) conjugated diene having from 4 to 5 carbon atoms or (2) para-methylstyrene; and (b) one or more curatives for said rubbery isobutylene polymer(s); wherein said bladder is of said butyl rubber composition as a cured rubber composition.

U.S. Pat. No. 7,144,236 discloses an expandable bladder for shaping a pneumatic tire to be mounted inside a tire curing machine, the expandable bladder having a toroidal configuration and comprising a pair of opposing annular beads and an expansion portion located between the pair of annular beads, the expansion portion comprising a central portion, shoulder portions, and sidewall portions, the central portion having a generally constant thickness, wherein, when the bladder is in a mounted but uninflated mode, the bladder being characterized by: beginning at a distance (x) from each end of the central portion, and between the opposing annular beads, the shoulder portions and sidewall portions have a gradually increasing thickness.

U.S. Pat. No. 7,128,545 B2 discloses an expandable bladder for shaping a pneumatic tire to be mounted inside a tire curing machine, the expandable bladder having a toroidal configuration and comprising a pair of opposing annular beads and an expansion portion located between the pair of annular beads, the expansion portion comprising a central portion, shoulder portions, and sidewall portions, wherein, when the bladder is in a mounted but uninflated mode, the bladder is characterized by the shoulder portions of the bladder having a first radius of curvature R1 significantly less than a radius of curvature Rc of the central portion and a second radius of curvature R2 located outside of the bladder, the second radius of curvature being located between the first radius of curvature R1 and the central portion radius of curvature Rc.

U.S. Pat. No. 8,057,204 B2 discloses an expandable bladder for shaping a pneumatic tire to be mounted in a tire curing press, the bladder in an unmounted, relaxed state comprises: a shaped body having a pair of opposed annular beads, said body further comprising a central portion, sidewall portions, and shoulder portions interposed between the central portion and the sidewall portions, wherein the body is defined by an outer contour surface and an inner contour surface, wherein the outer contour surface is shaped differently than the inner contour surface, wherein a bladder gauge of the central portion decreases from a center point to a minimum point located between the center point and the shoulder portion, and then the bladder gauge increases from said minimum point to a maximum point located axially inward of the shoulder portion.

U.S. Pat. No. 10,538,041 B2 discloses a tire curing bladder assembly comprising a cured tire curing bladder including a body and an air barrier layer disposed on the body, wherein the air barrier layer includes a phase separated blend of elastomer and thermoplastic resin.

Curing bladders have been improved over recent decades. However, cure bladders wear-out relatively quickly and need to be replaced in molds on a continuing basis. This naturally results in recurring material and labor costs. There also remains a continuing desire for cure bladders that provide for better heat transfer which would reduce cure cycle times and energy consumption. Curing bladders that provide better mold release characteristics also continue to be sought in the rubber product manufacturing industry.

It has been found that graphene can be included in the rubber formulation used in manufacturing cure bladders to improve mold release characteristics, heat transfer, and the service life of such cure bladders. Accordingly, cure bladders that contain graphene can be used longer without being replaced which reduces the cost of purchasing or making new cure bladders and the labor cost associated with installing new cure bladders in molds. The improved heat transfer attained by utilizing graphene in cure bladders also increases mold throughput and reduces energy costs. Such cure bladders that contain graphene also exhibit improved mold release characteristics.

The subject invention more specifically relates to a tire curing bladder comprising a hollow, tubular member having a tubular circumference extending around a tubular axis in an un-extended state, said tubular membrane member being inflatable to provide a circular circumference greater than the tubular circumference of the tubular member in the un-extended state, said tubular member being comprised of a butyl rubber and a graphene. The graphene can be beneficially incorporated into the butyl rubber with a fatty acid in the form of the graphene formulations of this invention.

The tire processing bladder is responsive to the introduction of fluid thereto under a range of fluid pressures for assuming a relatively uninflated state for insertion into a tire processing assembly and a relatively inflated state during tire processing carried out in said assembly, said bladder comprising a tubular shaped membrane of rubber composition formed along a tubular axis and having embedded therein a plurality of reinforcing cords traversing substantially parallel paths within said rubber composition in a generally spiral pattern about said tubular axis, and which cords as said bladder is inflated from said relatively uninflated towards said relatively inflated state by said introduction of fluid tend to become aligned away from said spiral pattern and more towards a longitudinal direction aligned with said tubular axis, said bladder forming a substantially toroid-shaped portion inside a tire being cured in said relatively inflated state inside said tire processing assembly, said substantially toroid-shaped portion tending to rotate into relatively close engagement with an inside surface of said tire being cured in response to said introduction of fluid, said cords protruding from said bladder when formed to have said substantially toroid-shaped portion to create reciprocal shallow areas between said cords and thus form a matrix for venting air trapped between said bladder and an uncured tire; wherein the rubber composition is comprised of a butyl rubber and graphene.

The subject invention also discloses a method of using an expandable rubber bladder to cure a hydrocarbon rubber, said method comprising: (1) inserting an uncured rubber composition into a curing mold having an expandable rubber bladder positioned therein and one or more molding surfaces, wherein the expandable bladder is comprised of a cured rubber formulation which is comprised of a butyl rubber and from about 1 to about 30 parts by weight of graphene; (2) closing the mold and expanding the bladder by application of a hot fluid in the internal portion of said bladder cavity to expand the bladder outwardly against an inner surface of the uncured hydrocarbon rubber to force said uncured hydrocarbon rubber against the one or more molding surface; (3) curing the hydrocarbon rubber under conditions of heat and pressure, (4) deflating said expandable bladder, and (5) removing the cured hydrocarbon rubber from said curing mold.

The rubber cure bladders of this invention are characterized by containing graphene. The graphene is a one-atom-thick crystalline form of carbon in which carbon atoms are held together by sigma bonds that are arranged in a two-dimensional honeycomb lattice. Graphene is a crystalline allotrope of carbon with 2-dimensional properties. The carbon atoms in graphene are densely packed in a regular atomic-scale hexagonal (chicken wire) pattern. Each atom has four bonds, one σ bond with each of its three neighbors and one Π-bond that is oriented out of plane. The distance between adjacent carbon atoms in graphene is approximately 0.142 nanometers.

The graphene used in the practice of this invention can have zig-zag, armchair, K-region, gulf, bay, cove, and fjord edge topologies. Typically, at least 50 percent, 60 percent, 70 percent, or 80 percent of the carbon-carbon bonds on the edges of the graphene structure will be in the zig-zag configuration, the armchair configuration, or the bay configuration. In many cases, at least 40 percent, 50 percent, or 60 percent of the carbon-carbon bonds on the edges of the graphene structure will be in the zig-zag configuration. In one embodiment at least 40 percent, 50 percent, or 60 percent of the carbon-carbon bonds on the edges of the graphene structure will be in the armchair configuration. In another embodiment at least 40 percent, 50 percent, or 60 percent of the carbon-carbon bonds on the edges of the graphene structure will be in the bay configuration. Typically, less than 40 percent of the carbon-carbon bonds on the edges of the graphene structure will be in the cove configuration and more typically less than 30 percent of the carbon-carbon bonds on the edges of the graphene structure will be in the cove configuration. In another embodiment less than 40 percent of the carbon-carbon bonds on the edges of the graphene structure will be in the cove configuration and less than 30 percent or more typically less than 20 percent of the carbon-carbon bonds on the edges of the graphene structure will be in the fjord configuration.

The graphene used in the practice of this invention is exfoliated into nano-scaled graphene plate (NGP) material that is essentially comprised of individual single sheets of graphene or a plurality of sheets of graphite planes. Each graphite plane, also referred to as a graphene plane or basal plane, is comprised of a two-dimensional hexagonal structure of carbon atoms. Each plane has a length and a width parallel to the graphite plane and a thickness orthogonal to the graphite plane characterized in that at least one of the values of length, width, and thickness is 100 nanometers (nm) or smaller. Preferably, all length, width and thickness values are smaller than 100 nm. This NGP material can be produced by a method described in U.S. Pat. No. 7,071,258 which comprises the steps of: (a) carbonization or graphitization to produce a polymeric carbon, (b) exfoliation or expansion of graphite crystallites in the polymeric carbon to delaminate or separate graphene planes, and (c) mechanical attrition of the exfoliated structure to nanometer-scaled plates. The teachings of U.S. Pat. No. 7,071,258 are incorporated herein by references for the purpose or describing graphene that can be utilized in the practice of this invention and methods for manufacturing such graphene. In the practice of this invention it is preferred for the graphene to be comprised of individual single sheets of graphene (single graphene planes or single basal planes).

U.S. Pat. No. 10,717,653 reveals a method for manufacturing graphene. This method comprises: (a) applying a vacuum to a furnace, the inside of the furnace comprising: (A) an oxygen scavenger; and, (B) a growth sample, the growth sample, comprising: a carbon-containing metal and a substrate, wherein the carbon-containing metal is in the form of a plurality of seeds that are in contact with the substrate; (b) introducing a hydrogen-containing gas to the furnace; (c) heating the inside of the furnace to a temperature and for a time sufficient to initiate graphene formation on the carbon-containing metal; (d) cooling the furnace; and (e) removing the seeds from the substrate.

U.S. Pat. No. 8,142,754 discloses a method for the production of graphene comprising: spacing a silicon wafer from a silicon carbide wafer in a pressure vessel; reducing the pressure in the vessel to vacuum; heating the silicon wafer to a first temperature to evaporate silicon from its opposing surface; while simultaneously, heating the silicon carbide wafer to a second temperature to anneal the silicon carbide wafer, wherein the first temperature is 1200° C. and the second temperature is at least about 1500° C. U.S. Pat. No. 9,388,048 describes a method for synthesizing monolayer graphene by chemical vapor deposition and U.S. Pat. No. 10,000,384 discloses a method for the laser direct synthesis of graphene. The teachings of U.S. Pat. Nos. 8,142,754, 9,388,048, and 10,000,384 are incorporated herein by reference for the purpose of describing techniques for manufacturing graphene.

The graphene is typically incorporated into the curing bladders of this invention at a level which is within the range of about 1 phr to about 30 phr (the term "phr" stands for parts by weight per 100 parts by weight of rubber). The graphene will more typically be incorporated into the cure bladders of this invention at a level which is within the range of 2 phr to 10 phr and which will normally be included at a level which is within the range of 3 phr to 7 phr. It is generally preferred for the graphene to be included in the cure bladders of this invention at a level which is within the range of 4 phr to 6 phr (about 5 phr). The graphene is added to the rubber formulation utilized in making the cure bladder during the mixing of the cure bladder formulation and is therefore dispersed throughout the molded bladder in a homogeneous manner. This can be carried out using standard rubber mixing techniques, such as in a Banbury mixer or a mill mixer.

The cure bladders of this invention are comprised of at least one butyl rubber. The butyl rubber, which is sometimes simply referred to as "butyl," is typically a synthetic copolymer of isobutylene and isoprene (an isobutylene-isoprene copolymer which can be abbreviated as IIR). Such IIB is typically comprised of about 0.5 weight percent to about 5 weight percent bound isoprene and from about 95 weight percent to about 99.5 weight percent bound isobutylene and is more typically comprised of 1 weight percent to 3 weight percent bound isoprene and from about 97 weight percent to about 99 weight percent bound isobutylene. In the alternative the butyl rubber can be a homopolymer of isobutylene (polyisobutylene or PIB).

As described in U.S. Pat. No. 5,538,218, a preferred rubber composition for use in one embodiment of this application is a copolymer of at least one iso-olefin and a para-alkylstyrene which is desirably brominated. The teachings of U.S. Pat. No. 5,538,218 are incorporated by references herein. The iso-olefins may have from 4 to 7 carbon atoms. The alkyl group of the para-alkylstyrene may have from 1 to 11 carbon atoms. In this embodiment of the invention at least 50 weight percent, more desirably at least 75, 80, 85 or 95 weight percent of the rubbers of the bladder formulation are one or more polymers having at least repeat units from one or more iso-olefin and a para-alkylstyrene. Desirably, the one or more iso-olefin is 80, 90, or 95 weight percent or more isobutylene. Desirably, the para-alkyl-styrene is 80, 90, or 95 weight percent or more para-methylstyrene. Desirably, the isobutylene polymer comprises is from 1 to 20 weight percent para-methylstyrene, and more desirably from 2 to 15 weight percent para-methylstyrene. Desirably, the isobutylene polymer comprises from 80 to 9.9 weight percent isobutylene and more desirably from 85 to 98 weight percent. Desirably, the bromine content is up to 5 weight percent and preferably from about 0.2 to 1.5 or 2.5 weight percent in the rubber. Diene monomers having 4 to 8 carbon atoms are optionally present up to 5 or 8 weight percent, desirably from 0.5 to 3 weight percent. The preferred copolymer of isobutylene and para-methylstyrene is essentially free of isoprene and other conjugated dienes. A highly preferred brominated butyl rubber is Exxpro™ with a Mooney Viscosity ML (1+8) at 125° C. of 50±5, an isobutylene content of 94 or 95 weight percent, and a para-methylstyrene content of about 5 weight percent, with a total bromine content of 0.8 weight percent. European Patent Application having Publication No. 0,344,021 describes how to make such polymers and is hereby incorporated by reference.

Optionally, other butyl rubbers may be used in combination with the isobutylene-para-methylstyrene copolymers or in lieu thereof. Desirably, at least 50 weight percent and more desirably at least 75, 80, 85 or 90 weight percent of all the rubbery polymers of the bladder composition are a butyl rubber polymer from isobutylene and one or more conjugated dienes, preferably isoprene. Desirably, the isoprene is from 1 to 5 weight percent and the remainder (e.g. from 95 to 99 weight percent) is isobutylene. These include butyl rubber, halogen substituted butyl rubbers such as chlorobutyl and bromobutyl. Small amounts (e.g. less than 10 or 20 weight percent of all rubbery polymers) of diene based elastomers such as neoprene rubber may be included as cure accelerators or for other purposes. Neoprene rubber is also known as poly(chloroprene). It is a common co-curative in resin cure systems as described below. In rubber formulations the neoprene is counted towards the 100 parts by weight rubber even though it has a separate function as a halogen containing elastomer. Desirably the 100 parts rubber of the cure bladders are at least 50, 75, 80, 85 or 90 weight percent polymers or copolymers of isobutylene.

The butyl rubber bladder can be cured with sulfur cure or resin cure systems. Sulfur cure systems are less preferred with isobutylene polymers having residual unsaturation as reversion and/or increasing modulus during use as a curing bladder can result. Representative resins for curing include conventional phenolic-resins used in an amount from 1 phr to 10 phr. A resorcinol or formaldehyde resin cure system is often used for such purposes. Such cure systems for bladder compositions are well known to those having skill in the art. For an example, see U.S. Pat. No. 3,031,423 which is hereby fully incorporated by reference. A resin cure system using phenol-formaldehyde, along with a small amount of sulfur is shown in Table I. Reactive phenolformaldehyde resins for curing butyl rubbers are commercially available and well known in the art.

The cured rubber composition of the curing bladder may also contain conventional additives including fillers, peptizing agents, stearic acid, accelerators, sulfur vulcanizing agents, reactive resins for curing, antiozonants, antioxidants, processing oils, activators, initiators, plasticizers, waxes, prevulcanization inhibitors, extender oils, and the like. If a sulfur cured system is used the amount of sulfur is desirably from 0.1 phr to 10 phr. Representatives of sulfur vulcanizing agents include sulfur; sulfur donating agents, for example amine disulfide, polymeric polysulfide, or sulfur olefin adducts. Preferably the amount of sulfur utilized as a curative will be within the range of 0.5 to 7 phr. Accelerators for sulfur cured systems may be used in amounts from 0.1 phr to 5 phr more desirably from 0.5 phr to 2.5 phr. These types of accelerators are well known and include amines, disulfides, guanidines, thioureas, thiols, thiazoles, thiurams, sulfenamides, dithiocarbamates and xanthates. As classes, many of these accelerators are either too fast or too slow for curing bladder systems but they may be used in small amounts or specific compounds in each group may be appropriate for use in curing bladders. Blends of two or more accelerators may also be used.

Fillers include reinforcing fillers such as carbon black which can be used in amounts which are within the range of about 25 phr to 85 phr and more typically within the range of 40 phr to 60 phr. Typical carbon blacks that can be used include acetylene blacks, N110, N121, N220, N231, N234, N242, N293, N299, N326, N330, M332, N339, N343, N347, N351, N358, N375, N472, N539, N550, N660, N683, N754, and N765.

Antioxidants and antiozonants may desirably be added to the curing bladder composition. Antioxidants prevent oxidative crosslinking or oxidative chain scission so that the modulus and fracture properties of the rubber are unchanged during exposure to oxidation especially at elevated temperatures. Antioxidants for rubber compounds in general and for butyl rubber more specifically are well known to the art. Desirable amounts are from 0.1 phr to 10 phr and more desirably from about 2 phr to 6 phr. Antiozonants are compounds that prevent chain scission due to exposure to ozone. They are also well known to the art. Antioxidants and antiozonants include monophenols, bisphenols, thiophenols, polyphenols, hydroquinone derivatives, phosphites, phosphate blends, thioesters, naphthylamines, diphenolamines, as well as other diaryl amine derivatives, para-phenylene diamines, quinolines and blended amines.

Fillers are desirably incorporated into the curing bladder formulation at levels which are within the range of 2 phr to 200 phr and more desirably from 30 phr to 100 phr. It is normally preferred for the filler to be included at a level which is within the range of 40 phr to 60 phr. A preferred filler is carbon black which is available in various particle sizes and with different surface reactivities from vendors such as Degussa. Reinforcing type fillers are preferred for use in curing bladders. Silica may be used in addition to carbon black. Silicas are generally described as precipitated silicas, fume silicas and various naturally occurring materials having substantial amounts of $SiO_2$ therein.

Various oils and waxes may be used in curing bladder formulation depending upon the compatibility of the oils and waxes with the butyl rubber and the other components of the rubber formulation. They may be uniformly dispersed or they may purposefully tend to phase separate from the composition (migrate to the surface). Waxes include microcrystalline wax and paraffin wax. Oils include aliphatic-naphthenic aromatic resins, polyethylene glycol, petroleum oils, ester plasticizers, vulcanized vegetable oils, pine tar, phenolic resins, petroleum resins, polymeric esters, and rosins. Oils and waxes can be used in amounts from 0.5 phr to 20 phr and more desirably from 1 phr to 10 phr. They are usually considered plasticizers and modulus modifiers. Fatty acids such as stearic acid, palmitic acid and oleic acid may be used in amounts from about 0.1 phr to 5 phr with a range of from about 0.2 phr to 1 phr being preferred. In one embodiment of this invention the cure bladder formulation is void of fatty acids, such as stearic acid. Zinc oxide may be present in amounts from about 0.5 phr to about 10 phr.

In various embodiments of this invention, the tire curing bladders are void of graphite, are void of carbon nanotubes (including single-walled carbon nanotubes and multi-walled carbon nanotubes), are void of layers of carbon filler, are void of buckminsterfullerene (Buckey balls), and are void of fatty acids (including stearic acid).

The curing bladder may be molded in an injection molding machine or a transfer molding machine. If transfer molding is selected the material from the Banbury is extruded as a slug. A cure meter is used to determine the approximate time to develop optimal cure at specific temperatures. The actual cure time will depend on heating rate and the gauge (thickness) of the curing bladder. The curing bladder desirably will have a toroidal shape and will typically be cured at a temperature which is within the range of about 150° C. to 200° for a period of about 45 minutes to 90 minutes.

The curing bladders of this invention are useful for molding and curing various hydrocarbon materials including pneumatic vehicle tires and miscellaneous pneumatic tires for non-vehicle applications. Other hydrocarbon articles cured in bladder equipped presses include hoses, various sleeves, and air springs (a shock absorbing spring for vehicles and certain industrial equipment). The curing bladders of this invention exhibit good lubricity, excellent mold release characteristics, provide excellent heat transfer, and provide for a long service life due to their enhanced lubricity. U.S. Pat. Nos. 4,877,469, 5,062,781, 7,128,545 B2, U.S. Pat. No. 7,144,236 B2, and U.S. Pat. No. 8,057,204 B2 disclose various tire cure bladder designs that can be manufactured utilizing the butyl rubber/graphene formulations of this invention. The teachings of U.S. Pat. Nos. 4,877,469, 5,062,781, 7,128,545 B2, U.S. Pat. No. 7,144,236 B2, and U.S. Pat. No. 8,057,204 B2 are incorporated herein by reference for the purpose of teaching tire cure bladder designs that can be used in the practice of this invention.

Typical properties of a curing bladder as produced are desirably a 300% Modulus of 4.0 to 8.0 MPa, a Breaking Strength of 5 to 14 MPa, an Elongation at Break of 400 to 1,000%, a Shore A Hardness of 35 to 65, a Hot Tension Set according to ASTMD412 at 16 hours at 50% elongation and 190° C. of 5% to 20%, and a Hot Peel Adhesion to a butyl rubber innerliner of 40 N to 100 N. More desirably the curing bladder has a 300% Modulus of 4 to 6, a Breaking Strength of 8 to 11 MPa, an Elongation at Break of 600 to 800, a Shore A hardness of 40 to 50, a Hot Tension Set of 12 to 17%, and a Hot Peel Adhesion of 45 to 90. The properties of a curing bladder after aging 24 hours at 177° C. desirably include an Elongation at Break of 300% to 800% more desirably 300% to 500%, a 300% Modulus of 4.5 to 7.5 MPa, a Breaking Strength of 4.5 to 7.5 MPa, a Shore A hardness of 55 to 65, a Hot Tension Set of 13.0 to 18.0% and a Coefficient of Friction with lubrication ASTMD4518 of 0.4 to 1.0.

The graphene compositions of this invention can also be used in making rubber bushings and expansion joints. For instance, rubber bushings are utilized in countless products as an interface between component parts therein to dampen vibration and reduce noise generated during use of the product. Rubber bushings are utilized in a wide array of products, including automotive products, aviation products, heavy equipment, industrial machinery, household products, musical instruments, sporting goods, bicycles, motorcycles, office machinery, electrical generation equipment, computer components, and many other products which have an interface between component parts thereof. In any case, the main purpose of rubber bushings is to act as a buffer and to absorb energy produced by the interaction of parts within the product. The rubber bushing separates the two components of the product while allowing for a limited amount of movement between the component parts with the level of vibration and noise generated being reduced. The component parts in such products can be made of wood, plastic, ceramics, fiberglass, metal, cement, and other types of materials.

U.S. Pat. No. 3,952,840 discloses an elastomeric bushing clearance device for a closed-loop disc brake. This patent more specifically reveals a disc brake for a wheeled vehicle, including: a rotatable braking disc; a stationary hydraulic cylinder having inner and outer pistons slidable in opposite directions which are substantially parallel to the axis of said braking disc, said pistons defining a fluid chamber therebetween into which fluid under pressure is supplied when braking; directly and indirectly actuated friction pad assemblies positioned adjacent to opposite faces of said braking disc, said directly actuated friction pad assembly being in abutting engagement with said inner piston which forces it against said braking disc when said inner piston is moved by said fluid; a yoke movable in a direction parallel to said axis of said braking disc by said outer piston to move said indirectly actuated friction pad assembly; and two guide means for guiding said yoke in said direction parallel to said axis of said disc to allow smooth engagement of said indirectly actuated friction pad assembly with said braking disc, each of said guide means including a support member provided with a bore therethrough and fixed to said yoke, a guide rod secured to a portion of said stationary hydraulic cylinder and passing through the bore of each said support member, said guide rod securely provided with a cylindrical collar around the periphery of said guide rod, the improvement comprising an elastomeric bushing tightly disposed between the inner surface of said bore of each said support member and the outer peripheral surface of said cylindrical collar and secured to each said support member, each said elastomeric bushing being, at its portion contacting the outer peripheral surface of said cylindrical collar, configured to slide on the outer peripheral surface of said cylindrical collar, in a direction for applying the brake, with a lower friction resistance than that in the reverse direction for releasing the brake U.S. Pat. No. 3,964,807 discloses a low friction bushing that is made by winding a continuous strand of bondable low friction thread impregnated with a bonding resin into the shape of a hollow cylinder having an axial length greater than the finished bushing. The cylinder is inserted into an annular cavity and with heat and pressure is axially compressed therewithin to radially expand it and compact the thread turns and fuse the resin into a solidified matrix with the thread and resin matrix completely filling the cavity and thereafter the solidified bushing is removed from the cavity. One of the cylindrical walls of the cavity is finished with a surface of bearing quality such that the surface of the bushing pressed thereagainst will be of a complementary quality. U.S. Pat. No. 3,964,807 more specifically reveals a low friction bushing comprising: a hollow cylindrical element consisting essentially of a plurality of layers of continuous turns of a strand of low friction thread comprised of bondable filaments and polytetrafluoro ethylene filaments, wherein the thread is impregnated with a bondable resin; said threads compressed together axially of the cylindrical element and held in radially expanded integrated relation by a matrix of solidified and cured bonding resin distributed throughout the layers; and one of the cylindrical surfaces of the hollow cylindrical element comprising a bearing surface of low friction thread presenting a substantially uniform layer of juxtaposed turns of the thread bonded together by said resin. In these bushings said hollow cylindrical element can include an external peripheral flange encircling the element and can be composed of said turns and bonding resin. It these bushings of bearing surface can be on the interior cylindrical surface of the hollow cylindrical element.

U.S. Pat. No. 4,235,482 discloses a bushing for providing a connection which supports a substantially unidirectional force between a pair of tensioned link members one of which has a bushing bore therein, comprising a rigid elongate core, a first elastomeric semicylinder having a predetermined wall thickness and a predetermined axial length bonded on substantially all of the inside surface thereof to one side of said rigid core, at least one additional elastomeric semicylinder having a wall thickness substantially greater than and a cumulative axial length substantially less than said predetermined wall thickness and axial length respectively when in an uncompressed state and being bonded on substantially all of the inside surface thereof to the other side of said rigid core, said first semicylinder and additional semicylinder being sized for a press fit in said bushing bore and assuming a compressed state therein such that the axis of said elongate core is substantially coincident with the axis of the bushing bore, whereby the bushing is retained frictionally within the bushing bore by the compression of said additional elastomeric semicylinder, and said first elastomeric semicylinder may withstand a predetermined radial force load without exceeding the endurance limit of the elastomer. This patent further describes a bushing used to pivotally couple adjacent links together and to withstand a force load therebetween and wherein one of the links has a bushing bore therein, said bushing comprising a rigid core member, a first elastomeric semicylinder having a predetermined axial length and predetermined radial wall thickness and being bonded at the inside surface thereof along one side of the outer surface of said rigid core member, at least two additional elastomeric semicylinders having a cumulative axial length less than said predetermined axial length and radial wall thicknesses greater than said predetermined radial wall thickness and being axially spaced along and bonded to the opposite side of the outer surface of said rigid core member, said elastomeric semicylinder radial wall thicknesses providing an interference fit with the bushing bore so that when said first and additional elastomeric semicylinders are pressed into the bushing bore with said first semicylinder on the side thereof to be compressed by the force load and said rigid core is coupled to the other of said links, said additional elastomeric semicylinders retain the bushing axially in the bore and said first elastomeric semicylinder accommodates a high force loading.

U.S. Pat. No. 5,080,332 discloses a vibration-proof rubber bushing, comprising: (a) a cylindrical metallic outer envelope coated with a rubber member at an outer periphery thereof and having a bottom portion and an engagement pawl projected at a predetermined position of a side wall portion of an inner peripheral surface of said outer envelope; (b) a viscous fluid filled in the outer envelope; (c) a first elastic member with an outer part on which a metallic ring member is adhered; and (d) a metallic inner envelope fitted into an inner portion of the outer envelope via the first elastic member and onto a part of an outer peripheral surface of said inner envelope where the first elastic member is adhered, seal projections being projected from the ring member, the ring member being engaged with the engagement pawl installed on the outer envelope, the outer envelope being drawn at its side wall portion opposing the seal projections so that the seal projections of the inner envelope are brought in close contact with the inner periphery of the outer envelope and the viscous fluid is completely sealed by the seal projections and the drawn side wall portion of the outer envelope.

U.S. Pat. No. 5,190,269 discloses a rubber bushing, comprising: an inner cylindrical member having roughened portions formed on a part of an outer peripheral surface thereof; a ring comprising resin, said ring disposed integrally on said part of said outer peripheral surface on which said roughened portions are formed, said ring having a non-circular shape comprising a non-circular cross-section taken in a radial direction with respect to a cylindrical axis of said inner member; an elastic member comprising rubber, said elastic member formed outside said inner cylindrical member; an outer cylindrical member connected to said inner cylindrical member by means of said elastic member; and said non-circular shape of said ring including at least two projections which project in an axially symmetrical manner in directions perpendicular to said cylindrical axis of said inner cylindrical member. U.S. Pat. No. 5,190,269 further reveals a rubber bushing comprising: a metal inner cylindrical member, a ring disposed integrally on an outer peripheral surface of said inner cylindrical member and having a non-circular radial cross-section, an elastic rubber member formed on an outside surface of said inner cylindrical member, and an outer cylindrical member connected to said inner cylindrical member and said ring by means of said elastic member; wherein a part of said outer peripheral surface of said inner cylindrical member has a roughened surface, and said ring is a resin ring molded on said roughened surface; said ring including two diametrically opposed radial projections extending outward therefrom and surrounded by said elastic member. Additionally, this patent describes a rubber bushing, comprising: an inner cylindrical member having roughened portions formed on a part of an outer peripheral surface thereof; a ring comprising resin, said ring disposed integrally on said part of said outer peripheral surface on which said roughened portions are formed, said ring having a non-circular shape comprising a non-circular cross-section taken in a radial direction with respect to a cylindrical axis of said inner member; an elastic member comprising rubber, said elastic member formed outside said inner cylindrical member; an outer cylindrical member connected to said inner cylindrical member by means of said elastic member; and said elastic member further including depressions formed at both ends thereof and which descend from free ends of said inner cylindrical member and ascend to free ends of said outer cylindrical member so as to form built-up portions on the free ends of said outer cylindrical member.

U.S. Pat. No. 5,328,160 discloses an improved bushing for bearing column loads including an inner metal tube surrounded by an elastomer cylinder and a flanged ferrule press-fit into the metal tube at one tube end, the flange of the ferrule overlying a selected portion of an end surface of the elastomer cylinder, wherein the improvement therewith comprises the tube having a cylindrical wall defining a longitudinal axis along which said column loads are borne and a seam extending in the tube wall parallel to the axis; and an adhesive at the interface of the metal tube and the ferrule.

U.S. Pat. No. 8,465,010 discloses a vibration damping rubber bushing adapted for installation between two components to be linked in a vibration damped manner comprising: an inner cylindrical member having opposite axial end faces, at least one of the axial end faces adapted to be pushed against one of the two components; a main rubber elastic body bonded to an outer circumferential face of the inner cylindrical member and adapted to be connected at an outer circumferential face side thereof to another of the two components; a plurality of anti-slip projections provided on the at least one of the axial end faces of the inner cylindrical member that project axially outward from the axial end face and extend with ribbed shape in a diametrical direction on the axial end face to produce a spokewise pattern overall; and an annular water barrier projection provided on a diametrical medial section of the at least one of the axial end faces of the inner cylindrical member, projecting axially outwardly and extending circumferentially, with the anti-slip projections being disposed to both radially inner side and radially outer side of the annular water barrier projection, wherein the anti-slip projections extend linearly in the diametrical direction from points in proximity to a radially inside edge to points in proximity to a radially outside edge of the at least one of the axial end faces of the inner cylindrical member, and wherein recesses that extend in the diametrical direction are respectively present between the anti-slip projections that are circumferentially adjacent, and the annular water barrier projection extends across these recesses in the circumferential direction at medial sections thereof in the diametrical direction.

U.S. Pat. No. 10,023,727 describes a rubber bushing composition comprising: 100 parts by weight of natural rubber; 20 to 30 parts by weight of a fast extruding furnace (FEF), a high abrasion furnace (HAF), or a mixture thereof as a filler; 0.5 to 1.5 parts by weight of 2,2,4-trimethyl-1, 2-dihydroquinoline (TMQ) and 1 to 2 parts by weight of N-isopropyl-N'-phenyl-p-phenylenediamine (IPPD) as an antioxidant; 0.8 to 1.5 parts by weight of a sulfur crosslinker; 0.5 to 2 parts by weight of N-cyclohexyl 2-benzothiazole sulfenamide (CBS) and 0.2 to 1 part by weight of tetramethylthiuram disulfide (TMTD) as a crosslinking accelerator; and 3 to 5 parts by weight of zinc oxide and 1.5 to 3 parts by weight of stearic acid as a crosslinking activator.

In general bushings are devices which are designed for reducing shocks, vibrations, and noise that is generated during the use of a product. They can be of many different designs that are engineered to provide the desired result in a particular product. Such bushings are widely used in automotive applications to reduce vibrations and noise that is generated as a vehicle travels over roadways and other surfaces that are frequently far for smooth. For example, the bushings include vehicle suspension systems to prevent vibration caused by hitting cracks and potholes in road surfaces from being transmitted to passengers and to improve vehicle handling. For example, bushings are used in vehicles as a stabilizer which promotes driving stability by reducing rolling generated while the vehicle is turning and for alleviating shock or vibrations introduced to the vehicle body by tires, and the like. In addition to suspension systems, bushings are widely used by the automotive industry in anti-roll bars, shock absorber mountings, double wishbone suspensions, gear sticks and engines.

Rubber bushings offer the advantage of excellent vibration isolation due to elasticity and their ability to absorb energy by converting it into heat. However, rubber bushings do inherently have a number of drawbacks. The biggest problem associated with rubber bushings is that they wear out over time. More specifically, rubber bushings can deteriorate due to environmental factors, such as exposure to heat, oxygen, ozone, oil, gasoline, and the like. Rubber bushings also deteriorate over time due to breakdown caused by mechanical forces, including abrasion and fatigue failure. Since worn-out bushings are frequently difficult and costly to replace, it would be highly desirable for them to provide an extended service life. Accordingly, there has been a long felt need for rubber bushings having excellent fatigue endurance and resistance to deterioration due to environmental factors.

The incorporation of graphene into rubber formulations used in expansion joints also provides valuable unexpected benefits. U.S. Pat. No. 3,936,080 discloses pipeline expansion joints having a smooth bore, for use with pipelines into which flow slurries containing solids in suspension, comprises a first sleeve open at both ends and having a tapered portion formed in the inner wall of one of its ends extending at a small angle with the axis of the first sleeve and over a substantial portion of the length of the first sleeve from its inside diameter to substantially its outside diameter, and a second sleeve also open at both ends and having a first portion of substantially the same inner diameter as the outer diameter of the first sleeve and telescopically mounted on the above-mentioned one end of the first sleeve, a second portion of the same diameter as the first sleeve, and an intermediate portion expanded at a small angle with the axis of the second sleeve over a substantial portion of its length from the second to the first portion of such second sleeve. This expansion joint has a smooth bore throughout with no area of abrupt changes in order to prevent turbulence and the resulting wear due to the solids in suspension in the slurries.

U.S. Pat. No. 4,030,740 discloses an expansion joint for two ducts comprising: first and second opposed conduits mounted onto an inner sleeve, said first conduit being slidably mounted onto said inner sleeve and said second conduit including means affixing said second conduit to said inner sleeve; and, said opposed conduits having outwardly extending receiving means on facing ends with an outer sleeve extending around said ends thereof, the outwardly extending means of the first conduit includes a flexible packing material therein sealingly engaging said first conduit and said outer sleeve, said first conduit being in sliding relation with said outer sleeve, said second conduit including means affixed against movement relative to said outer sleeve, said outer sleeve being in two sections, a first section and a second section, said first and second sections having opposed facing flanges thereon, said facing flanges including connecting means whereby said packing material may be removed and replaced.

U.S. Pat. No. 4,071,994 discloses an expansion joint for roofs and the like, especially for the sheet-metal flashing or cover plates of the finial, cresting or ridge of flat roofs, comprises a pair of metal strips defining an expansion gap between them. The gap is bridged on the underside of the joint with an elastomeric sealing band bonded, e.g., by vulcanization, to the metal strips and covered, on its side turned toward the environment with an intermediate metal strip slidingly held in place by the elastomeric band so as not to impede relative displacements of the first two metal strips upon thermal expansion and contraction. This patent more specifically reveals an expansion joint for structures adapted to be exposed to the ambient environment, comprising: a pair of first sheet-metal strips having confronting longitudinal edges defining a gap between them, said strips having outwardly turned faces on a side of the joint exposed to the environment and inwardly turned faces; an elastomeric sealing band spanning said gap bonded continuously to both of said strips along the inwardly turned faces thereof and alongside said longitudinal edges, said band forming with said first strips a water-tight seal; and a second sheet-metal strip bridging said gap and retained by said band against said first strips with freedom of sliding movement between said second strip and said first strips along said longitudinal edges and covering said band along said side of said joint, thereby shielding said band from the environment, said sealing band being vulcanized to said first strips along regions spaced from but parallel to said longitudinal edges, said second strip overlapping each of said first strips along said longitudinal edges.

U.S. Pat. No. 4,111,682 discloses an expansion joint for bridges and the like has an elastomeric member having areas of increased compressibility towards each edge, and integral flanges at each edge for securing to bridge deck parts. The bridging member with its flanges is a continuous, constant cross-section, extrusion and is cut either in the factory, or on site, to lengths corresponding to the width of the bridge roadway. This patent more specifically reveals an expansion joint buried in a roadway and bridging a gap between adjacent deck parts of a civil engineering structure the roadway consisting essentially of a plurality of strata and the expansion joint being buried in at least one of said strata and at least one of said strata being continuous over the said expansion joint, the expansion joint including an elongate elastomeric joint member disposed transversely across the roadway, said joint member consisting essentially of elastomeric material and having a body and flange parts, the body having a lower surface which is supported at respective sides of a median plane on respective deck parts whereby a central portion of the body spans the gap between the deck parts, a debonding layer between said lower surface and said deck parts, said flange parts being secured in watertight manner to the respective deck parts at each lateral side of the body whereby to form with the body a continuous waterproof roof over the gap, the body and the flange parts being formed in an integral one-piece whole of the elastomeric material, and edge portions of the body being separated from the central portion thereof by regions of the body of greater lateral compressibility than that of the edge portions and the central portion.

U.S. Pat. No. 4,240,653 discloses flexible expansion joints utilized for coupling conduit pipes or pipelines for conveyance, supply, service and drainage of service water, sewage, industrial water, etc. are provided, which comprise a tubular flexible body portion and two side joint portions. The tubular flexible body portion comprises bias cord reinforcement layer(s) provided circumferentially at a "cord angle" of 10° to 45°. Alternatively, it may further comprise circumferential cord reinforcement layer(s) circumferentially provided at a "cord angle" of 0° to 25° inside the bias cord reinforcement, and a plurality of coaxial rigid rings. The flexible expansion joints have good pliability, flexibility, vibration absorbing property, internal and external pressure resistance, durability, anti-deformation property and the like.

U.S. Pat. No. 4,241,944 discloses a high-pressure, high temperature expansion joint having superior physical characteristics and susceptible of economical manufacture. The joint comprises inner and outer covering layers of elastomeric material and a body which includes at least one layer of a bias-cut fabric and at least one outer supporting layer formed of a helically-wound strip of elastomeric material with a plurality of parallel reinforcing strands running longitudinally through the strip. This expansion joint is formed in a shallow or flowing arch configuration which does not trap particulate materials in a fluid stream, and obviates the need for a filler piece. This patent more specifically discloses flexible expansion joint adapted to be secured between a pair of substantially rigid conduits and including first and second ends adapted to be received in sealing relationship with ones of said conduits and having an enlarged central section forming an arch, the walls of said arch extending radially at substantially less than 90° to the axis of the joint, the portion of said joint lying between said ends comprising an inner wall and an outer wall of elastomeric material, at least one support layer positioned intermediate said inner and outer walls and extending over the entire length of said joint between said first and second ends formed by a sheet of fabric oriented at a bias with respect to the axis of said joint, and at least one reinforcing layer positioned intermediate said inner and outer layers comprising a plurality of strands extending helically and continuously over substantially the entire length of the joint intermediate the ends thereof, such that no turns of any of said strands are disposed immediately adjacent other turns of the same strand.

U.S. Pat. No. 4,247,838 reveals an expansion joint for wave guides, said expansion joint including first and second aligned components which have the same inside dimensions as the wave guide and which are free to move longitudinally with respect to each other, the improvement wherein said first component comprises a tube, said second component includes a trap positioned at least partially between said components and radially outside the first component, the electric length of said trap being equal to half the wavelength of the central frequency transmitted by the wave guide, and means for separating said components longitudinally at the trap by a distance which varies as the length of the wave guide varies, and wherein said trap is folded so as to obtain two transmission lines which have the same electric length, and said trap includes a first transmission line constituted by a space comprised between the first component and the first longitudinal branch of the second component, a second transmission line constituted by a space comprised between said first branch and said second longitudinal branch, one of whose ends has a radially inwardly turned lip facing said other surface of said first component and covering one end of said first branch, and wherein said second transmission line is wider than that of the first transmission line and having therefore a greater impedance.

U.S. Pat. No. 4,279,533 discloses a roadway having concrete sections with upper surfaces aligned to form the roadway surface and spaced from each other to provide an expansion slot, each concrete section having at the end thereof adjacent said slot a recess which extends longitudinally of the slot and which has a bottom surface generally parallel to the roadway surface and a side surface extending from said bottom surface to the roadway surface; a metal plate bridging said slot, said metal plate being secured to the bottom surface of one of said recesses and being movable relative to the bottom surface of the other of said recesses; and a unitary elastomeric slab above said metal plate and bridging said slot, said elastomeric slab having an upper surface aligned with the upper surface of said concrete sections and having edge surfaces bonded to the side surfaces of said recesses, said elastomeric slab having a premolded center portion of relatively high elasticity and having edge portions which are molded in situ and which are of relatively low elasticity.

U.S. Pat. No. 4,374,442 discloses an expansion joint sealing assembly for sealing a gap between adjacent deck sections at the intersection of curb and roadway portions of said deck sections, said sealing assembly including a first pair of elongated elastomeric pads designed for placement on said roadway portions of said deck sections along opposite sides of said gap, a second pair of elongated elastomeric pads designed for placement on said curb portions of said deck sections on opposite sides of said gap, an elongated flexible membrane member designed to extend across said gap between both said curb portions and said roadway portions of said deck sections, said flexible membrane member having longitudinally extending side edge portions designed to be secured between said pads and said deck sections, and means to secure said elongated pads to said deck sections with said side edge portions of said membrane member held between said pads and said deck sections, said assembly characterized by the improvement comprising: (a) said side edge portions of said flexible membrane member each having molded convolutions with laterally extending axes, (b) each of said convolutions having an upwardly facing first rounded portion with a locking rib projecting upwardly from said first rounded portion, each of said locking ribs extending longitudinally of said membrane member and being separated from adjacent locking ribs by downwardly facing second rounded portions of said convolutions, and (c) said elongated elastomeric pads each having downwardly facing slots extending longitudinally of the respective pad, said locking ribs on said membrane member fitting within said slots in said elastomeric pads to hold said convoluted side edge portions of said membrane member in place between said pads and said deck sections.

U.S. Pat. No. 5,044,835 discloses an expansion joint for use in constructing concrete structures, the expansion joint comprising a plurality of sandwich type composite plates, each composite plate comprising a sheet-like elastic body sandwiched between a pair of hard plates with a rib at an end of each of said hard plates, said ribs being connected to each other by a connection means and a water-swelling rubber disposed between said composite plates.

U.S. Pat. No. 6,176,526 relates to an expansion joint to connect two or more concentric bodies that are heated/cooled to different temperatures for the passage of liquid or gases. When the connecting portion is at an angle not in plane with the concentric bodies, the design allows for the gravity drainage of fluids and slurries from one connecting body to another without pooling or damming.

U.S. Pat. No. 9,631,759 discloses an expansion joint for connecting pipe elements, said expansion joint comprising: a tube having an inner surface defining an inner diameter, an outer surface surrounding said inner surface and first and second ends oppositely disposed; an inlet segment having a smooth inner surface, an outlet end connected to said first end of said tube, and an inlet end oppositely disposed therefrom, said outlet end having an inner diameter that is smaller than an inner diameter of said inlet end, said inner diameter of said outlet end being equal to said inner diameter of said tube, said inlet segment being connected to said tube by an externally mounted mechanical coupling; a sleeve having first and second ends oppositely disposed, said sleeve being positioned surrounding at least a portion of said tube, said portion including said second end of said tube, said sleeve having a constant inner diameter over its entire longitudinal length, said inner diameter being larger than an outer diameter of said tube; a ring, separate from said sleeve and removably attachable to said first end thereof, said ring surrounding said tube and having an inner surface facing said outer surface of said tube, said ring supporting said sleeve on said tube only at said first end of said sleeve; at least one inwardly facing circumferential groove positioned in the inner surface of said ring; at least one bearing element positioned within said at least one groove; an externally mounted coupling positioned circumferentially around a portion of both said ring and said first end of said sleeve, said coupling removably attaching said ring to said sleeve; a seal mounted on said inner surface of said ring and sealingly engaging said outer surface of said tube, said ring and said sleeve being slidably movable axially relatively to said tube; a hoop attached to said ring and surrounding said tube and positioned radially and longitudinally between said ring and said tube, said hoop being positioned adjacent to a packing material, said packing material being captured between said hoop and a shoulder of said ring.

U.S. Pat. No. 9,739,049 discloses expansion joint system for imposition under compression between a first substrate and a second substrate, the first substrate and the second substrate being substantially co-planar with a first plane, the first substrate being distant the second substrate by a first distance, comprising: an elongated core, the elongated core composed of a resiliently compressible foam, the elongated core having an elongated core longitudinal axis, the elongated core having an elongated core longitudinal length, the elongated core having an elongated core top, the elongated core having an elongated core bottom, the elongated core having an elongated core height intermediate the elongated core top and the elongated core bottom, the elongated core having an elongated core first side, the elongated core first side being generally perpendicular to the elongated core top, the elongated core having an elongated core second side, the elongated core second side being generally perpendicular to the elongated core top; the elongated core having an elongated core lateral width, the elongated core lateral width configured to be greater than the first distance prior to imposition, and at least one longitudinal load-transfer member, the at least one longitudinal load-transfer member being incompressible, the at least one longitudinal load-transfer member having a longitudinal load-transfer member axis, the elongated core longitudinal axis and the longitudinal load-transfer member axis being parallel, the at least one longitudinal load-transfer member having longitudinal load-transfer member length, the elongated core longitudinal length and longitudinal load-transfer member length being equivalent, the at least one longitudinal load-transfer member bonded to the elongated foam core at the elongated core top, the at least one longitudinal load-transfer member having a longitudinal load-transfer member lateral width, wherein the longitudinal load-transfer member lateral width is not more than one-fourth the first distance; and wherein the at least one longitudinal load-transfer member is proximate a middlemost portion of the elongated foam core between the elongated core first side and the elongated core second side.

U.S. Pat. No. 9,249,911 discloses flexible expansion joint for connecting a first pipe and a second pipe such that the first pipe and the second pipe are movable and bendable relative to each other, said flexible expansion joint comprising: a first sleeve to be put on an end part of the first pipe; an outer sleeve to be put on an end part of a second pipe so as to overlap the first sleeve and capable of moving axially relative to the first sleeve; a first sealing member sealing a gap between the inside surface of the first sleeve and the outside surface of the first pipe in a liquid-tight sealed state such that the first sleeve and the first pipe are axially movable relative to each other; a second sealing member sealing a gap between the inside surface of the outer sleeve and the outside surface of the second pipe in a liquid-tight sealed state such that the outer sleeve and the second pipe are axially movable relative to each other; a third sealing member sealing a gap between the outside surface of the first sleeve and the inside surface of the outer sleeve in a liquid-tight sealed state such that the first sleeve and the outer sleeve are axially movable relative to each other; a first length limiter including a first reference member placed on the first pipe, a first reference holder formed on the first sleeve, and a first stopper for limiting the axial movement of the first pipe and the first sleeve relative to each other to a predetermined first limit length, the first sealing member being unable to maintain the gap between the inside surface of the first sleeve and the outside surface of the first pipe in a liquid-tight sealed state when a distance between the first reference member and the first reference holder exceeds the predetermined first limit length; and a second length limiter including a second reference member placed on the second pipe, a second reference holder formed on the outer sleeve, and a second stopper for limiting the axial movement of the second pipe and the outer sleeve relative to each other to a predetermined second limit length, the second sealing member being unable to maintain the gap between the inside surface of the outer sleeve and the outside surface of the second pipe in a liquid-tight sealed state when a distance between the second reference member and the second reference holder exceeds the predetermined second limit length, wherein the first stopper, when the first reference holder moves toward an end face of the end part of the first pipe with respect to the first reference member, limits the first reference holder from moving toward the end face of the end part of the first pipe such that the distance between the first reference member and the first reference holder does not exceed the predetermined first limit length, and the second stopper, when the second reference holder moves toward an end face of the end part of the second pipe with respect to the second reference member, limits the second reference holder from moving toward the end face of the end part of the second pipe such that the distance between the second reference member and the second reference holder does not exceed the predetermined second limit length.

As is the case with rubber bushings, rubber expansion joints also wear out over time. More specifically, rubber expansion joints can deteriorate due to environmental factors, such as exposure to heat, oxygen, ozone, oil, gasoline, and the like. Rubber expansion joints also deteriorate over time due to breakdown caused by mechanical forces, including abrasion and fatigue failure. Since worn-out expansion joint can be difficult or impossible to replace it would be highly desirable for them to provide an extended service life. Accordingly, there has been a long felt need for rubber expansion joints having excellent fatigue endurance and resistance to deterioration due to environmental factors.

The present invention is based upon the discovery that graphene can be included in the rubber formulation used in manufacturing bushings and expansion joints to improve the durability and physical properties thereof. This invention more specifically discloses a rubber bushing which is comprised of a flexible component and a rigid component which are adapted to provide an interface between two parts of an apparatus to dampen vibration and/or noise, said flexible component being comprised of a cured rubber and graphene.

The subject invention also reveals an article having an expansion joint therein wherein the article is comprised of a first rigid component and a second rigid component, wherein the first rigid component and the second rigid component are connected through an expansion joint which is comprised of a cured rubber and graphene.

The rubber bushings and expansion joints of this invention are characterized by containing graphene. The graphene is a one-atom-thick crystalline form of carbon in which carbon atoms are held together by sigma bonds that are arranged in a two-dimensional honeycomb lattice. Graphene is a crystalline allotrope of carbon with 2-dimensional properties. The carbon atoms in graphene are densely packed in a regular atomic-scale hexagonal (chicken wire)

pattern. Each atom has four bonds, one σ bond with each of its three neighbors and one Π-bond that is oriented out of plane. The distance between adjacent carbon atoms in graphene is approximately 0.142 nanometers.

The graphene used in the practice of this invention can have zig-zag, armchair, K-region, gulf, bay, cove, and fjord edge topologies. Typically, at least 50 percent, 60 percent, 70 percent, or 80 percent of the carbon-carbon bonds on the edges of the graphene structure will be in the zig-zag configuration, the armchair configuration, or the bay configuration. In many cases, at least 40 percent, 50 percent, or 60 percent of the carbon-carbon bonds on the edges of the graphene structure will be in the zig-zag configuration. In one embodiment at least 40 percent, 50 percent, or 60 percent of the carbon-carbon bonds on the edges of the graphene structure will be in the armchair configuration. In another embodiment at least 40 percent, 50 percent, or 60 percent of the carbon-carbon bonds on the edges of the graphene structure will be in the bay configuration. Typically, less than 40 percent of the carbon-carbon bonds on the edges of the graphene structure will be in the cove configuration and more typically less than 30 percent of the carbon-carbon bonds on the edges of the graphene structure will be in the cove configuration. In another embodiment less than 40 percent of the carbon-carbon bonds on the edges of the graphene structure will be in the cove configuration and less than 30 percent or more typically less than 20 percent of the carbon-carbon bonds on the edges of the graphene structure will be in the fjord configuration.

The graphene used in the practice of this invention is exfoliated into nano-scaled graphene plate (NGP) material that is essentially comprised of individual single sheets of graphene or a plurality of sheets of graphite planes. Each graphite plane, also referred to as a graphene plane or basal plane, is comprised of a two-dimensional hexagonal structure of carbon atoms. Each plane has a length and a width parallel to the graphite plane and a thickness orthogonal to the graphite plane characterized in that at least one of the values of length, width, and thickness is 100 nanometers (nm) or smaller. Preferably, all length, width and thickness values are smaller than 100 nm. This NGP material can be produced by a process the method described in U.S. Pat. No. 7,071,258 which comprising the steps of: (a) carbonization or graphitization to produce a polymeric carbon, (b) exfoliation or expansion of graphite crystallites in the polymeric carbon to delaminate or separate graphene planes, and (c) mechanical attrition of the exfoliated structure to nanometer-scaled plates. The teachings of U.S. Pat. No. 7,071,258 are incorporated herein by references for the purpose or describing graphene that can be utilized in the practice of this invention and methods for manufacturing such graphene. In the practice of this invention it is preferred for the graphene to be comprised of individual single sheets of graphene (single graphene planes or single basal planes).

U.S. Pat. No. 10,717,653 reveals a method for manufacturing graphene. This method comprises: (a) applying a vacuum to a furnace, the inside of the furnace comprising: (A) an oxygen scavenger; and, (B) a growth sample, the growth sample, comprising: a carbon-containing metal and a substrate, wherein the carbon-containing metal is in the form of a plurality of seeds that are in contact with the substrate; (b) introducing a hydrogen-containing gas to the furnace; (c) heating the inside of the furnace to a temperature and for a time sufficient to initiate graphene formation on the carbon-containing metal; (d) cooling the furnace; and (e) removing the seeds from the substrate.

U.S. Pat. No. 8,142,754 discloses a method for the production of graphene comprising: spacing a silicon wafer from a silicon carbide wafer in a pressure vessel; reducing the pressure in the vessel to vacuum; heating the silicon wafer to a first temperature to evaporate silicon from its opposing surface; while simultaneously, heating the silicon carbide wafer to a second temperature to anneal the silicon carbide wafer, wherein the first temperature is 1200° C. and the second temperature is at least about 1500° C. U.S. Pat. No. 9,388,048 describes a method for synthesizing monolayer graphene by chemical vapor deposition and U.S. Pat. No. 10,000,384 discloses a method for the laser direct synthesis of graphene. The teachings of U.S. Pat. Nos. 8,142,754, 9,388,048, and 10,000,384 are incorporated herein by reference for the purpose of describing techniques for manufacturing graphene.

The graphene is typically incorporated into the bushings and expansion joints of this invention at a level which is within the range of about 1 phr to about 80 phr (the term "phr" stands for parts by weight per 100 parts by weight of rubber). The graphene will more typically be incorporated into the bushings and expansion joints of this invention at a level which is within the range of 2 phr to 50 phr and which will normally be included at a level which is within the range of 3 phr to 30 phr. It is generally preferred for the graphene to be included in the bushings and expansion joints of this invention at a level which is within the range of 4 phr to 10 phr (about 5 phr). The graphene is added to the rubber formulation utilized in making the bushings and expansion joints of this invention during the mixing of the rubber formulation and is therefore dispersed throughout the rubber of the bushing or the expansion join in a homogeneous manner. This can be carried out using standard rubber mixing techniques, such as in a Banbury mixer or a mill mixer.

A wide variety of natural and synthetic rubbers can be used in making the rubber bushings and the expansion joints of this invention. For instance, the rubber can be natural rubber, synthetic polyisoprene rubber, low vinyl polybutdiene rubber, medium vinyl polybutadiene rubber, high vinyl polybutadiene rubber, high cis-1,4-polybutadiene rubber, solution styrene-butadiene rubber, emulsion styrene-butadiene rubber, styrene-isoprene rubber, styrene-isoprene-butadiene rubber, nitrile rubber, carboxylated nitrile rubber, neoprene rubber, ethylene-propylene rubber, ethylene-propylene-diene rubber (EPDM), butyl rubber, halobutyl rubber, polynorbornene rubber, and various mixtures thereof.

The energy absorbing rubbery compositions described in U.S. Pat. No. 4,504,604 are particularly useful in manufacturing vibration and noise dampening bushings. These rubber compositions are comprised of (1) a polynorbornene rubber, (2) 20 phr 400 phr (parts by weight per 100 parts by weight of rubber) of a plasticizer, and (3) 20 phr to 70 phr of a hydrogenated pine tar resin. The plasticizer is typically comprised of (a) an oil having a polar content of less than about 4 weight percent and an absorptivity at 260μ, as determined by ASTM Method D2008 of about 8 or less and (b) an aromatic resin. The oil contains from about 20 to about 50 weight percent aromatic compounds and no more than about 1 weight percent or 2 weight percent polar compounds. The oil also typically has a molecular weight ranging from about 200 to about 600 and preferably has a molecular weight ranging from about 300 to 450. The aromatic resin normally is a polymer of a vinyl-substituted aromatic compound containing from 8 to 16 carbon atoms and wherein said aromatic resin has a molecular weight of about 200 to about 800 and preferably has a molecular weight ranging from 300 to 500. For example, the aromatic resin can be a polyterpene having a molecular weight ranging from about 200 to about 800 and preferably having a molecular weight ranging from 300 to 500. Polystyrene is another example of a preferred aromatic resin. Such energy absorbing rubber compositions are further described in U.S. Pat. No. 4,504,604 and the teachings of U.S. Pat. No. 4,504,604 are incorporated herein by reference.

The cured rubber composition employed in making the bushings and expansion joints of this invention may also contain conventional additives including fillers, peptizing agents, stearic acid, accelerators, sulfur vulcanizing agents, reactive resins for curing, antiozonants, antioxidants, processing oils, activators, initiators, plasticizers, waxes, prevulcanization inhibitors, extender oils, and the like. If a sulfur cured system is used the amount of sulfur is desirably from 0.1 phr to 10 phr. Representatives of sulfur vulcanizing agents include sulfur; sulfur donating agents, for example amine disulfide, polymeric polysulfide, or sulfur olefin adducts. Preferably the amount of sulfur utilized as a curative will be within the range of 0.5 to 7 phr. Accelerators for sulfur cured systems may be used in amounts from 0.1 phr to 5 phr more desirably from 0.5 phr to 2.5 phr. These types of accelerators are well known and include amines, disulfides, guanidines, thioureas, thiols, thiazoles, thiurams, sulfenamides, dithiocarbamates and xanthates. As classes, many of these accelerators are either too fast or too slow for curing the bushings and expansion joints of this invention, but they may be used in small amounts or specific compounds in each group may be appropriate for use in bushings and/or expansion joints. Blends of two or more accelerators may also be used.

Fillers include reinforcing fillers such as carbon black which can be used in amounts which are within the range of about 25 phr to 85 phr and more typically within the range of 40 phr to 60 phr. Typical carbon blacks that can be used include acetylene blacks, N110, N121, N220, N231, N234, N242, N293, N299, N326, N330, M332, N339, N343, N347, N351, N358, N375, N472, N539, N550, N660, N683, N754, and N765.

Antioxidants and antiozonants may desirably be added to the rubber composition. Antioxidants prevent oxidative crosslinking or oxidative chain scission so that the modulus and fracture properties of the rubber are unchanged during exposure to oxidation especially at elevated temperatures. Antioxidants for rubber compounds in general and for butyl rubber more specifically are well known to the art. Desirable amounts are from 0.1 phr to 10 phr and more desirably from about 2 phr to 6 phr. Antiozonants are compounds that prevent chain scission due to exposure to ozone. They are also well known to the art. Antioxidants and antiozonants include monophenols, bisphenols, thiophenols, polyphenols, hydroquinone derivatives, phosphites, phosphate blends, thioesters, naphthylamines, diphenolamines, as well as other diaryl amine derivatives, para-phenylene diamines, quinolines and blended amines.

Fillers are desirably incorporated into the rubber formulation at levels which are within the range of 2 phr to 200 phr and more desirably from 30 phr to 100 phr. It is normally preferred for the filler to be included at a level which is within the range of 40 phr to 60 phr. A preferred filler is carbon black which is available in various particle sizes and with different surface reactivities from vendors, such as Degussa. Reinforcing type fillers are preferred for use in bushings and expansion joints of this invention. Silica may be used in addition to carbon black. Silicas are generally described as precipitated silicas, fume silicas and various naturally occurring materials having substantial amounts of $SiO_2$ therein.

Various oils and waxes may be used in rubber formulations for bushings and expansion joints in accordance with this invention depending upon the compatibility of the oils and waxes with the butyl rubber and the other components of the rubber formulation. They may be uniformly dispersed or they may purposefully tend to phase separate from the composition (migrate to the surface). Waxes include microcrystalline wax and paraffin wax. Oils include aliphatic-naphthenic aromatic resins, polyethylene glycol, petroleum oils, ester plasticizers, vulcanized vegetable oils, pine tar, phenolic resins, petroleum resins, polymeric esters, and rosins. Oils and waxes can be used in amounts from 0.5 phr to 20 phr and more desirably from 1 phr to 10 phr. They are usually considered plasticizers and modulus modifiers. Fatty acids such as stearic acid, palmitic acid and oleic acid may be used in amounts from about 0.1 phr to 5 phr with a range of from about 0.2 phr to 1 phr being preferred. In one embodiment of this invention the rubber formulation is void of fatty acids, such as stearic acid. Zinc oxide may be present in amounts from about 0.5 phr to about 10 phr.

In various embodiments of this invention, the rubber formulation used in making the rubber portion of the bushing or the expansion joint will be void of graphite, carbon nanotubes (including single-walled carbon nanotubes and multi-walled carbon nanotubes), layers of carbon filler, buckminsterfullerene (Buckey balls), and fatty acids (including stearic acid).

Virtually any type of rubber bushings can benefit from including graphene in its rubber formulation. Some representative examples of such bushings that can benefit from incorporating graphene in the rubber formulations thereof are described in U.S. Pat. Nos. 3,952,840, 3,964,807, 4,235,482, 5,080,332, 5,190,269, 5,328,160, and 8,465,010. The teachings of U.S. Pat. Nos. 3,952,840, 3,964,807, 4,235,482, 5,080,332, 5,190,269, 5,328,160, and 8,465,010 are incorporated herein by reference.

Tubular rubber bushings can greatly benefit from incorporating graphene in the rubber components thereof. Such a split ring tubular bushing is illustrated in FIG. 1. This split ring tubular bushing is comprised of a cylindrical inner core, two split rings, and a rubber component which is situated between the cylindrical inner core and the two split rings. The cylindrical inner core and the split rings are comprised of a rigid material, such as a metal or a hard plastic. In some cases the rubber component will be surrounded by three or more split ring components.

Figure 2:
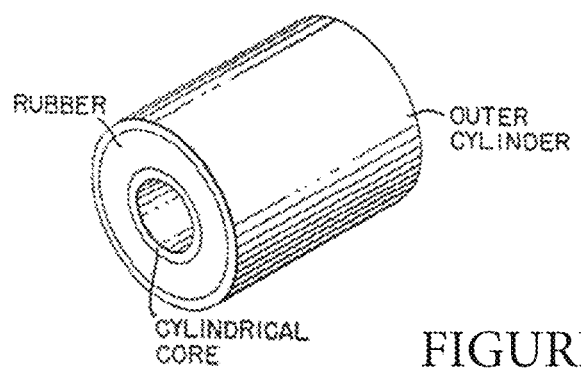
FIG. 2 depicts a tubular bushing having a cylindrical inner core, an outer cylinder, and a rubber component which is situated between the cylindrical inner core and the outer cylinder.

FIG. 2 depicts a tubular bushing having a cylindrical inner core, an outer cylinder, and a rubber component which is situated between the cylindrical inner core and the outer cylinder. In this type of bushing the cylindrical inner core is comprised of a rigid material, such as a metal or a hard plastic and the outer cylinder is comprised of a material which is rigid but which provides some degree of flexibility.

Figure 3:
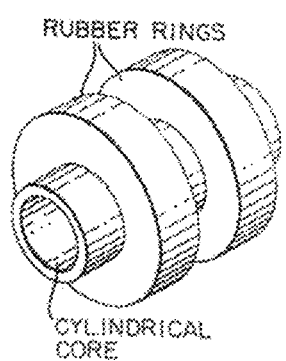
FIG. 3 illustrates a third type of tubular bushing.

In a third type of tubular bushing as shown in FIG. 3, a series of two or more rubber rings cover a cylindrical core and are spaced apart to allow for lateral expansion during compaction. In this type of tubular bushing the cylindrical is again comprised of a rigid material, such as a metal or a hard plastic.

Figure 4:
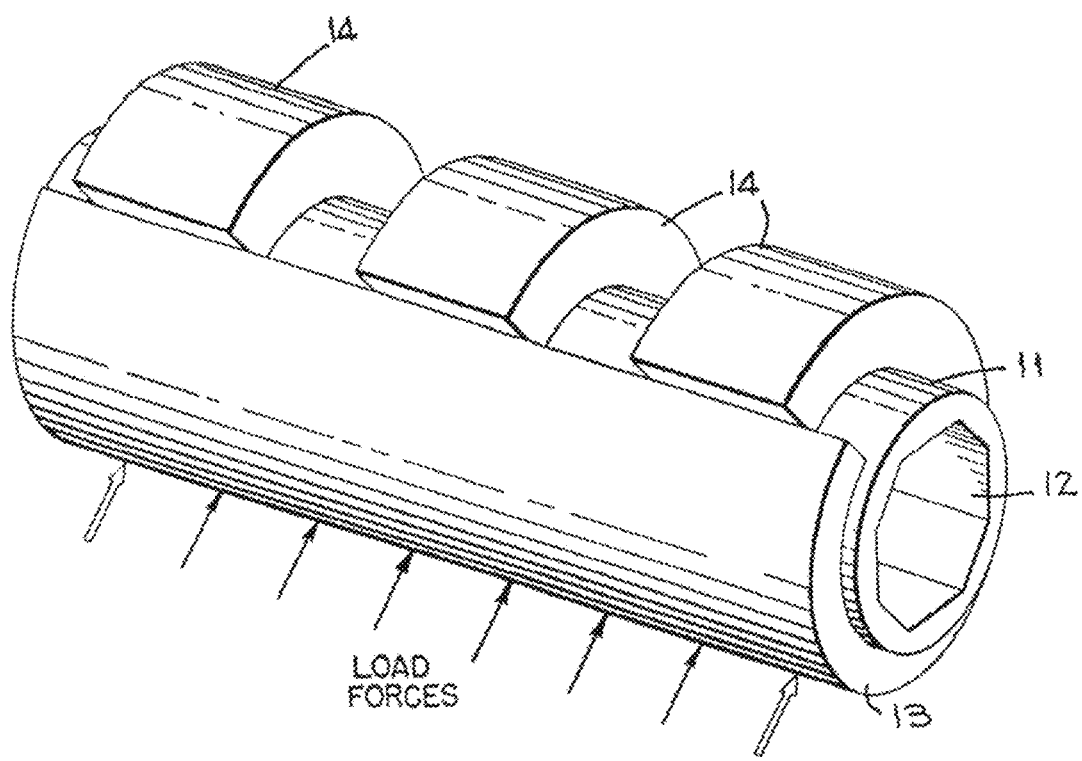
FIG. 4 illustrates a fourth type of tubular bushing.

A fourth type of tubular bushing is depicted in FIG. 4. This type of bushing includes a rigid cylindrical hollow core 11 which in this embodiment has an eight-sided inner surface 12. An elastomeric semicylinder 13 is bonded along one side of the outer surface of the cylindrical core 11. A number of shorter elastomeric semicylinders 14 are bonded in uniformly spaced relationship along the opposite side of the outer surface of the cylindrical core 11. The number of short semicylinders 14 will depend upon the radial wall thickness and the spacing therebetween as well as the extent of permissible deformation before the elastomeric material thereof ruptures internally. The elastomer used for both the long semicylinder 11 and the shorter semicylinders 14 is of a substance which dissipates very little energy internally when flexed cyclically. One of the best materials for use in the bushing of this invention is natural rubber which includes graphene as a filler. It should be noted that in the type of tubular bushing that the radial wall thickness of the long elastomeric semicylinder 13 is not as great as the radial wall thickness of the short elastomeric semicylinders 14. In general, the ratio of the cumulative length of the short semicylinders 14 to the length of the long semicylinder 13 is substantially the same as the ratio of the radial wall thickness of the long semicylinder to the radial wall thickness of each of the short semicylinders. For example, if the wall thickness of the long semicylinder is 60% of the wall thickness of the shorter semicylinders, the cumulative length of the short semicylinders will be approximately 60% of the overall length of the long semicylinder. As mentioned hereinbefore, the number of short semicylinders 14 will depend upon the axial length of the bushing and the capability of the elastomeric material to migrate when deformed without internal rupture.

Virtually any type of rubber expansion joint can benefit from including graphene in its rubber formulation. Some representative examples of such expansion joints are disclosed in U.S. Pat. Nos. 3,936,080; 4,030,740; 4,058,947; 4,071,994; 4,111,582; 4,240,653; 4,241,944; 4,247,838; 4,279,533; 4,279,954; 4,346,542; 4,374,442; 4,736,558; 4,058,947; 5,044,835; 5,385,953; 5,411,216; 5,424,118; 5,472,750; 5,513,925; 5,514,722; 5,536,110; 5,605,721; 6,176,526; 9,249,911; 9,631,759; 9,739,049; and U.S. Design Pat. No. 285,006. The teachings of U.S. Pat. Nos. 3,936,080; 4,030,740; 4,058,947; 4,071,994; 4,111,582; 4,240,653; 4,241,944; 4,247,838; 4,279,533; 4,279,954; 4,346,542; 4,374,442; 4,736,558; 4,058,947; 5,044,835; 5,385,953; 5,411,216; 5,424,118; 5,472,750; 5,513,925; 5,514,722; 5,536,110; 5,605,721; 6,176,526; 9,249,911; 9,631,759; 9,739,049; and U.S. Design Pat. No. 285,006 are incorporated herein by reference for the purpose of disclosing expansions joints having rubber components that can benefit from utilizing graphene as a filler therein.

Figure 5:
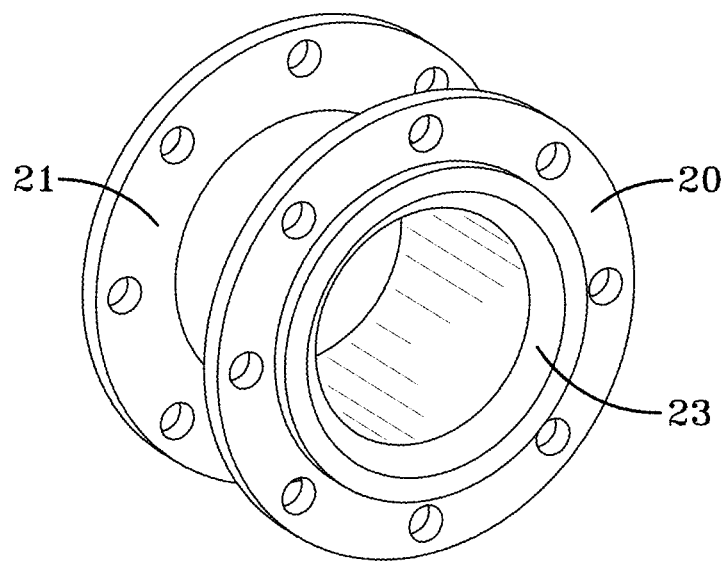
FIG. 5 illustrates a pipe expansion joint which includes a first end coupling on a first end of a tubular shaped rubber expansion component and a second end coupling of the second end of the tubular shaped rubber expansion component.
Figure 6:
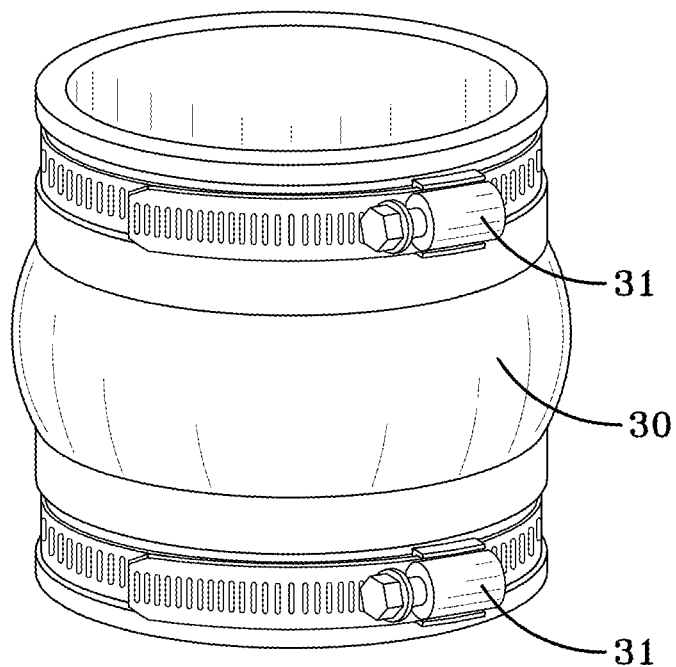
FIG. 6 illustrates an expansion pipe having a single arch.

Pipe expansion joints are widely used in a wide variety of applications. Such an expansion joint is illustrated in FIG. 5. This expansion joint includes a first end coupling 20 on a first end of a tubular shaped rubber expansion component 23 and a second end coupling 21 of the second end of the tubular shaped rubber expansion component 23. A wide variety of rubbers can be utilized in making the tubular shaped rubber expansion component 23 with nitrile rubber being preferred in applications where the expansion pipe might come in contact with oils or other organic liquids. It is generally preferred for the tubular shaped rubber expansion component 23 to be comprised of an EPDM rubber in applications where it will be exposed to elevated temperatures. An expansion pipe having a single arch 30 is depicted in FIG. 6. As can be seen the rubber expansion component 31 is adapted to be clamped onto pipes it is designed to connect using conventional hose clamps 32.

Figure 7:
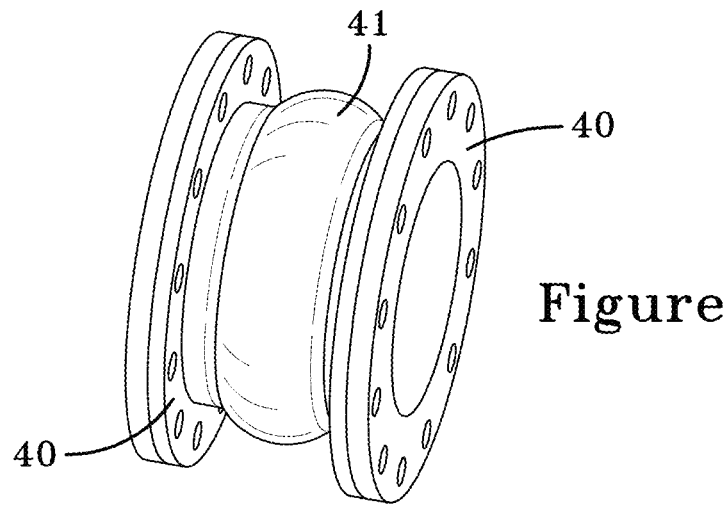
FIG. 7 illustrates a pipe expansion joint including a coupling wherein the expansion joint has one arch.
Figure 8:
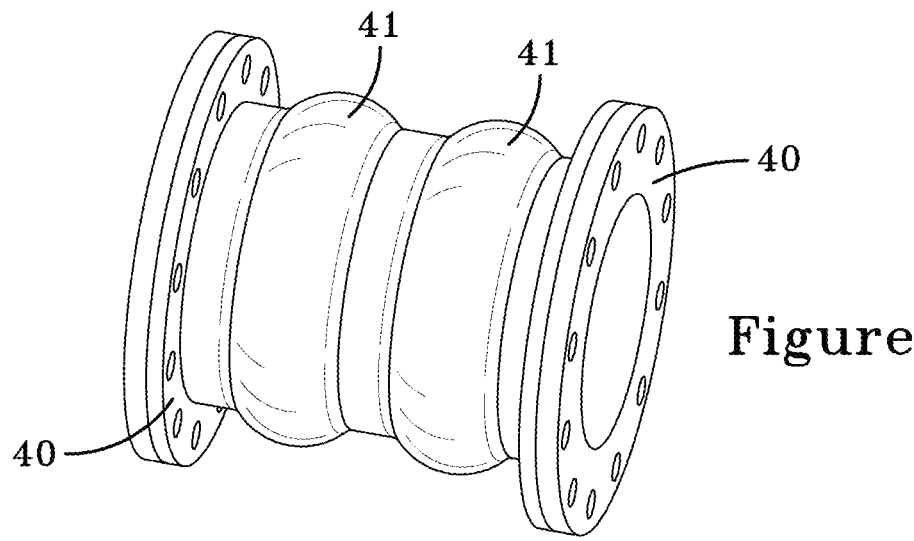
FIG. 8 illustrates a pipe expansion joint including a coupling wherein the expansion joint has two arches.
Figure 9:
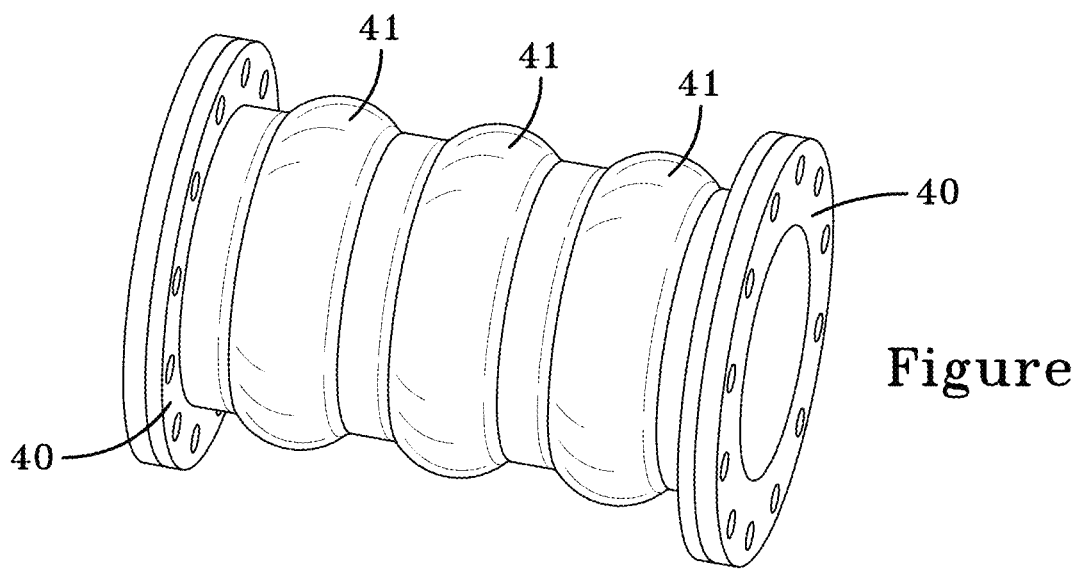
FIG. 9 illustrates a pipe expansion joint including a coupling wherein the expansion joint has three arches.

FIG. 7, FIG. 8, and FIG. 9 illustrate pipe expansion joints that include couplings 40 that are adapted to making a connection to desired pipes. These pipe expansions joints have one, two, or three arches 41 as illustrated in FIG. 7, FIG. 8, and FIG. 9, respectively. The arches allow the expansion joint to expand to a greater degree than would be possible without them.

Example 1

A tire cure bladder formulation can be made in accordance with this invention by mixing in an internal mixer the following constituents, based upon 100 parts by weight of butyl rubber:
  100 parts of Exxon Grade 268 butyl rubber,
  5 parts of graphene,
  5 parts of polychloroprene rubber,
  50 parts of carbon black
  5 parts of paraffinic oil,
  1 part of stearic acid,
  5 parts of zinc oxide, and
  10 parts of octyl phenol curing resin.

Example 2

In this experiment 30 grams of stearic acid was heated in a beaker to a temperature of about 180° F. at which temperature it melted. Then, 10 grams of graphene was mixed into the molten stearic acid with a stirring rod while it was maintained at the elevated temperature. The dispersion of the graphene in the stearic acid was then cooled to room temperature. The dispersion recovered was in the form of a hard solid clump. It was subsequently ground into hard small bits or pellets. These bits or pellets of the graphene dispersion are useful for the purpose of incorporating graphene into polymeric compositions where it is also desirable to include stearic acid in the polymeric formulation. This can be done at a temperature which is above the melting point of the stearic acid which is normally conventional in making most polymeric formulations.

Example 3

In this experiment 30 grams of stearic acid was heated in a beaker to a temperature of about 180° F. at which temperature it melted. Then, 30 grams of graphene was mixed into the molten stearic acid with a stirring rod while it was maintained at the elevated temperature. The dispersion of the graphene in the stearic acid was then cooled to room temperature with stirring being continued during the cooling process. The dispersion recovered was in the form of hard solid bits or particles. These bits or pellets of the graphene dispersion are useful for the purpose of incorporating graphene into polymeric compositions where it is also desirable to include stearic acid in the polymeric formulation. This can be done at a temperature which is above the melting point of the stearic acid which is normally conventional in making most polymeric formulations.

Example 4

In this experiment 30 grams of stearic acid was heated in a beaker to a temperature of about 180° F. at which temperature it melted. Then, 90 grams of graphene was mixed into the molten stearic acid with a stirring rod while it was maintained at the elevated temperature. The dispersion of the graphene in the stearic acid was then cooled to room temperature with stirring being continued during the cooling process. The dispersion recovered was in the form of solid particles which did not form dust when poured through the air from one beaker into another beaker. These solid graphene particle dispersions are useful for the purpose of incorporating graphene into polymeric compositions where it is also desirable to include stearic acid in the polymeric formulation. This can be done at a temperature which is above the melting point of the stearic acid which is normally conventional in making most polymeric formulations.

Example 5

In this experiment 30 grams of stearic acid was heated in a beaker to a temperature of about 180° F. at which temperature it melted. Then, 150 grams of graphene was mixed into the molten stearic acid with a stirring rod while it was maintained at the elevated temperature. The dispersion of the graphene in the stearic acid was then cooled to room temperature with stirring being continued during the cooling process. The dispersion recovered was in the form of solid particles which did not form dust when poured through the air from one beaker into another beaker. These solid graphene particle dispersions are useful for the purpose of incorporating graphene into polymeric compositions where it is also desirable to include stearic acid in the polymeric formulation. This can be done at a temperature which is above the melting point of the stearic acid which is normally conventional in making most polymeric formulations.

Example 6

A tire cure bladder formulation can be made in accordance with this invention using the solid graphene particle dispersion made in Example 4. In this procedure the solid graphene particle dispersion is mixed in an internal mixer with the following constituents, based upon 100 parts by weight of butyl rubber:
100 parts of Exxon Grade 268 butyl rubber,
12 parts of the graphene particle composition of Example 5,
5 parts of polychloroprene rubber,
50 parts of carbon black
5 parts of paraffinic oil,
1 part of stearic acid,
5 parts of zinc oxide, and
10 parts of octyl phenol curing resin.

Example 7

A tire cure bladder formulation can be made in accordance with this invention using the solid graphene particle dispersion made in Example 5. In this procedure the solid graphene particle dispersion is mixed in an internal mixer with the following constituents, based upon 100 parts by weight of butyl rubber:
100 parts of Exxon Grade 268 butyl rubber,
6 parts of the graphene particle composition of Example 5,
5 parts of polychloroprene rubber,
50 parts of carbon black
5 parts of paraffinic oil,
1 part of stearic acid,
5 parts of zinc oxide, and
10 parts of octyl phenol curing resin.

While certain representative embodiments and details have been shown for the purpose of illustrating the subject invention, it will be apparent to those skilled in this art that various changes and modifications can be made therein without departing from the scope of the subject invention.

What is claimed is:

1. A graphene composition comprising graphene and a fatty acid containing from 18 to 24 carbon atoms and having a melting point which is above about 140° F., wherein the graphene composition contains from about 0.25 parts by weight to 10 parts by weight of graphene per part by weight of the fatty acid, wherein the graphene composition is in the form of particles, and wherein said composition is further comprised of an alkyl lactate having an alkyl group containing for 2 to 10 carbon atoms.

2. The graphene composition of claim 1 wherein the fatty acid is stearic acid.

3. The graphene composition of claim 1 wherein the graphene composition contains 0.5 parts by weight to 8 parts by weight of graphene per part by weight of the fatty acid.

4. The graphene composition of claim 1 wherein the alkyl lactate is selected from the group consisting of ethyl lactate, iso-propyl lactate, n-propyl lactate, iso-butyl lactate, n-butyl lactate, t-butyl lactate, and isoamyl lactate.

5. The graphene composition of claim 1 wherein the alkyl lactate is present at a level which is within the range of 0.01 to 2 parts per parts per part by weight of the fatty acid.

6. A method for making a graphene composition which comprises (1) mixing graphene into the fatty acid or mixture of fatty acids containing from 18 to 24 carbon atoms at a temperature which is above the melting point of the fatty acid; (2) dispersing of the graphene into the fatty acid to produce a liquid dispersion; (3) cooling the liquid dispersion to below the melting point of the fatty acid to form a solid composition; and (4) pulverizing the solid composition into particles of the graphene composition having the desired particle size range.

7. The method of claim 6 which further comprises cooling the liquid dispersion to below the melting point of the fatty acid under agitation to form the graphene composition having the desired particle size range.

8. The method of claim 6 wherein the fatty acid is stearic acid.

9. The method of claim 6 wherein said composition is further comprised of an alkyl lactate having an alkyl group containing for 2 to 10 carbon atoms.

10. The method of claim 9 wherein the alkyl lactate is selected from the group consisting of ethyl lactate, iso-propyl lactate, n-propyl lactate, iso-butyl lactate, n-butyl lactate, t-butyl lactate, and isoamyl lactate.

11. The method of claim 9 wherein the alkyl lactate is isoamyl lactate and wherein the isoamyl lactate is present at a level which is within the range of 0.01 to 2 parts per part by weight of the fatty acid.

12. The method of claim 6 wherein the graphene is mixed into the fatty acid at a temperature which is within the range of 157° F. to 250° F.

13. The method of claim 6 wherein the graphene is mixed into the fatty acid at a temperature which is within the range of 160° F. to 220° F.

14. The method of claim 6 wherein the graphene is mixed into the fatty acid at a temperature which is within the range of 165° F. to 200° F.

15. The method of claim 6 wherein 0.25 parts by weight to 10 parts by weight of the graphene is dispersed into the fatty acid.

16. The method of claim 6 wherein 1 parts by weight to 6 parts by weight of the graphene is dispersed into the fatty acid.

17. A method for dispersing graphene into a polymeric formulation which comprises mixing the graphene composition of claim 1 into a polymer, wherein the mixing is conducted at a temperature which is above the melting point of the fatty acid.

18. The method of claim 17 wherein the polymer is a plastic.

19. The method of claim 17 wherein the polymer is an elastomer.

20. The method of claim 17 wherein the polymer is a thermoplastic elastomer.

* * * * *